(12) United States Patent
Murakami

(10) Patent No.: US 9,687,185 B2
(45) Date of Patent: Jun. 27, 2017

(54) BIOLOGICAL COMPONENT-MEASURING UNIT

(71) Applicant: NIKKISO CO., LTD., Tokyo (JP)

(72) Inventor: Motoaki Murakami, Tokyo (JP)

(73) Assignee: NIKKISO CO., LTD., Tokyo (JP)

(*) Notice: Subject to any disclaimer, the term of this patent is extended or adjusted under 35 U.S.C. 154(b) by 0 days.

(21) Appl. No.: 14/708,114

(22) Filed: May 8, 2015

(65) Prior Publication Data
US 2015/0238133 A1    Aug. 27, 2015

Related U.S. Application Data

(62) Division of application No. 12/089,265, filed as application No. PCT/JP2006/307237 on Apr. 5, 2006, now abandoned.

(30) Foreign Application Priority Data

Oct. 5, 2005 (JP) .................................. 2005-293069

(51) Int. Cl.
*G01N 15/06* (2006.01)
*C12Q 1/68* (2006.01)
(Continued)

(52) U.S. Cl.
CPC .... *A61B 5/150992* (2013.01); *A61B 5/14532* (2013.01); *A61B 5/157* (2013.01);
(Continued)

(58) Field of Classification Search
USPC .......... 436/8, 43, 50; 435/287.1; 422/44, 50, 422/99; 604/4.01, 19
See application file for complete search history.

(56) References Cited

U.S. PATENT DOCUMENTS

| 4,069,968 A | 1/1978 | Herman |
| 4,083,777 A | 4/1978 | Hutchisson |
| (Continued) | | |

FOREIGN PATENT DOCUMENTS

| EP | 0 372 074 A1 | 6/1990 |
| EP | 0 611 227 A1 | 8/1994 |
| (Continued) | | |

OTHER PUBLICATIONS

Office Action issued in U.S. Appl. No. 12/089,265 dated Feb. 9, 2011.
(Continued)

*Primary Examiner* — Dean Kwak
(74) *Attorney, Agent, or Firm* — McDermott Will & Emery LLP

(57) ABSTRACT

A biological component-measuring unit comprises a substrate detachably mountable on a medical support device; fluid channels disposed on the substrate, the fluid channels comprising a biological component-measuring channel; and an engaging mechanism configured to detachably engage with the medical support device so that the biological component-measuring unit is attached to and detached from the medical support device. The biological component-measuring channel includes: a first fluid transferring section disposed on the biological component-measuring channel and configured to be engaged with and actuated by a first fluid transfer structure disposed on the medical support device and transfer a sample fluid in one direction in cooperation with the first fluid transfer structure, when the biological component-measuring unit is mounted on the medical support device.

11 Claims, 12 Drawing Sheets

(51) Int. Cl.
  *B01L 3/00* (2006.01)
  *A61B 5/15* (2006.01)
  *A61F 2/02* (2006.01)
  *A61M 1/36* (2006.01)
  *A61B 5/145* (2006.01)
  *A61B 5/157* (2006.01)
  *A61B 50/13* (2016.01)
  *C12M 1/34* (2006.01)
  *A61B 10/00* (2006.01)
  *G01N 35/00* (2006.01)
  *A61B 5/1495* (2006.01)

(52) U.S. Cl.
  CPC .. *A61B 5/150022* (2013.01); *A61B 5/150221* (2013.01); *A61B 5/150305* (2013.01); *A61B 5/150358* (2013.01); *A61B 5/150755* (2013.01); *A61B 50/13* (2016.02); *A61F 2/022* (2013.01); *A61M 1/36* (2013.01); *A61M 1/3621* (2013.01); *A61M 1/3638* (2014.02); *B01L 3/508* (2013.01); *A61B 5/1495* (2013.01); *A61B 5/14542* (2013.01); *A61B 5/14546* (2013.01); *A61B 10/0045* (2013.01); *A61M 2230/201* (2013.01); *B01L 2200/10* (2013.01); *B01L 2200/12* (2013.01); *B01L 2200/141* (2013.01); *B01L 2300/123* (2013.01); *B01L 2400/0481* (2013.01); *G01N 2035/00148* (2013.01)

(56) References Cited

U.S. PATENT DOCUMENTS

| | | |
|---|---|---|
| 4,585,007 A | 4/1986 | Uchigaki et al. |
| 4,637,813 A | 1/1987 | DeVries |
| 5,697,899 A | 12/1997 | Hillman et al. |
| 6,200,287 B1 | 3/2001 | Keller et al. |
| 6,695,803 B1 * | 2/2004 | Robinson ............... A61M 1/02 210/252 |
| 2002/0085952 A1 * | 7/2002 | Ellingboe ........... A61M 1/3621 422/45 |
| 2004/0167457 A1 | 8/2004 | Tonelli et al. |

FOREIGN PATENT DOCUMENTS

| | | |
|---|---|---|
| EP | 1 950 568 A1 | 7/2008 |
| JP | 62-186846 | 8/1987 |
| JP | 06-094669 | 4/1994 |
| JP | 06-292722 | 10/1994 |
| JP | 07-213604 | 8/1995 |
| JP | 11-500029 A | 1/1999 |
| JP | 03-131240 B2 | 1/2001 |
| JP | 2001-504748 A | 4/2001 |
| JP | 2003-518964 A | 6/2003 |
| JP | 2004-109099 A | 4/2004 |
| JP | 2006-058280 A | 3/2006 |
| WO | 01/37786 A2 | 5/2001 |

OTHER PUBLICATIONS

Office Action issued in U.S. Appl. No. 12/089,265 dated Jun. 23, 2011.

\* cited by examiner

BIOLOGICAL COMPONENT-MEASURING UNIT

CROSS-REFERENCE TO PRIOR APPLICATION

This is a Divisional Application of application Ser. No. 12/089,265 filed on Apr. 4, 2008, which is a U.S. national phase application under 35 U.S.C. §371 of International Patent Application No. PCT/JP2006/307237 filed Apr. 5, 2006, which claims the benefit of Japanese Patent Application No. 2005-293069 filed Oct. 5, 2005, both of which are incorporated by reference herein. The International Application was published in Japanese on Apr. 12, 2007 as WO 2007/039946 A1 under PCT Article 21 (2).

TECHNICAL FIELD

The present invention relates to a biological component-measuring unit, a biological component-measuring unit package, a medical support instrument kit, and medical support instrument kit package. More particularly, the present invention relates to a biological component-measuring unit that can be easily attached to a medical support device proper, which leads to the improvement of workability. The clinical examiner is capable of measuring biological components, such as blood sugar levels, by hygienically operating the unit. The present invention also relates to a package of a biological component-measuring unit capable of preserving a biological component-measuring unit in a sterile condition for a long time, which package allows a biological component-measuring unit, preserved in a sterile condition, to be taken out when the unit is used. The present invention further relates to a medical support instrument kit that can be easily fitted to a medical support device proper, which leads to the improvement of workability. The clinical examiner is capable of measuring biological components, such as blood sugar levels, by hygienically operating the kit. Members and parts that contact fluids, other than the medical support device proper, can be arranged in the kit, which makes the preparation for operating the device easier. The present invention further relates to a package of a medical support instrument kit, capable of preserving a medical support instrument kit in a sterile condition for a long time, which package allows a medical support instrument kit, preserved in a sterile condition, to be taken out when the kit is used.

BACKGROUND ART

Conventional devices used in ICUs, such as an artificial endocrine pancreas device, require the connection of various tubes to the device, which connection includes, for example, the one between the tubes of an instrument to take a body fluid sample from a living body and the designated pipe of an ICU device. Because many tubes are used to connect various vessels inside and around an ICU device with various device units inside and around the ICU device, it takes the operator a long time to connect all the tubes. Also, because the tubes are contaminated with body fluids, there is a probability that operators and/or patients may become infected through the accidental exchange of body fluids in the hospital.

In view of these situations, desired are instruments for measuring blood sugar levels, used in clinical devices such as an artificial endocrine pancreas, which enable the operator to connect tubes accurately and easily, and to operate the clinical devices hygienically, free from the probability of nosocomial infection.

As an example of the module in which tubing for measuring components of a blood is completed prior to a clinical examination in the hospital, proposed is "an integrated blood treatment fluid module (10; 210), having: a support member (20; 220); a blood treatment device (40; 240) mounted on the support member (20; 220); and, a plurality of fluid circuits (50, 60, 70, 80, 90, 100; 250, 260, 270, 280, 290) interconnected with the support member (20; 220), at least one of the fluid circuits (50, 60, 70, 80, 90, 100; 250, 260, 270, 280, 290) being disposed in a U-shape relative to the support member (20; 220) with each U-shaped portion (54, 84, 94, 104; 254, 264, 274, 284) extending from the support member (20; 220) for being adapted to cooperate with a peristaltic pump, and at least one of the fluid circuits (50, 60, 70, 80, 90, 100; 250, 260, 270, 280, 290) being fluidly connected to the blood treatment device (40; 240)." See JP 6-292722 (1994) A ("JP '722").

However, JP '722 does not teach the measurement of the glucose component in blood. Although JP '722 describes sensors for measuring some components in blood, which is a blood treatment device, this document provides the blood treatment device with the following definition: 'As used herein, the term "blood treatment device" means any device for removing components from and/or introducing components into a blood stream, including plasmapheresis, oxygenation, hemodialysis, hemofiltration and hemodiafiltration treatment device.' See paragraph [0006] of JP '722. As understood, the device disclosed in this prior art document is a device used for hemodialysis.

Also, JP '722 is silent about calibrating sensors to measure the components in blood.

Disclosure of the Invention

The present invention intends to solve the problems associated with conventional technologies. The objective of the present invention is to provide a biological component-measuring unit such as a blood sugar-level-measuring unit that can be easily attached to a medical support device proper, which leads to the improvement of workability and which enables the clinical examiner to measure biological components, such as blood sugar levels, by hygienically operating the unit; a package for a biological component-measuring unit, such as a package for a blood sugar-level-measuring unit; a medical support instrument kit, enabling the clinical examiner to easily and hygienically carry out an operation to make a medical support device ready for work; and a package for a medical support instrument kit.

An embodiment for solving the problems described above is a biological component-measuring unit having a substrate detachably mountable on a medical support device proper, and fluid channels fixed to the substrate, the medical support device proper including a fluid transfer structure for making fluids in the fluid channels flow in one direction in cooperation with the fluid channels, wherein the fluid channels include a biological component-measuring channel which is:

(1) attachable to and detachable from a body fluid-drawing channel for drawing a fluid that has been sampled through a body fluid sampler;

(2) capable of transferring the fluid in the biological component-measuring channel in one direction, in cooperation with the fluid transfer structure, once the substrate is mounted on the medical support device proper;

(3) provided with a biological component sensor for measuring a biological component included in the fluid being transferred; and (4) capable of discharging the fluid as a waste liquid after the completion of the measurement of the biological component by the biological component sensor.

Another embodiment is a biological component-measuring unit including a substrate detachably mountable on a medical support device proper, and fluid channels fixed to the substrate, the medical support device proper including fluid a transfer structure for making fluids in the fluid channels flow in one direction in cooperation with the fluid channels, wherein the fluid channels comprises a biological component-measuring channel which is:
(1) attachable to and detachable from a body fluid-drawing channel for drawing a fluid that has been sampled through a body fluid sampler;
(2) capable of transferring the fluid in the biological component-measuring channel in one direction, in cooperation with the fluid transfer structure, once the substrate is mounted on the medical support device proper;
(3) detachably coupled to a sample-introducing channel through which the fluid is transferred to a biological component sensor for measuring a biological component included in the fluid being transferred, and a sample-discharging channel through which the fluid is discharged from the biological component sensor; and
(4) capable of discharging the fluid as a waste liquid after the completion of the measurement of the biological component by the biological component sensor, and the fluid channels support the biological component sensor in measuring the biological components.

Yet another embodiment is a biological component-measuring unit according to the first means or the second means, the fluid channels further having a diluent-supplying channel which
(1) is detachably coupled to a diluent-drawing channel through which a diluent stored in a diluent storage tank is drawn;
(2) makes it possible to transfer the diluent in the diluent-supplying channel in one direction in cooperation with the fluid transfer structure, once the substrate is mounted on the medical support device proper; and
(3) makes it possible to supply the diluent to a part upstream of the biological component sensor in the biological component-measuring channel.

An aspect of the biological component-measuring unit includes the biological component-measuring channel is provided with a mixing gadget for mixing the body fluid with the diluent supplied through the diluent-supplying channel.

Yet another embodiment is a biological component-measuring unit where the fluid channels further include a gas channel which
(1) is capable of introducing air;
(2) makes it possible to transfer gas in the gas channel in one direction in cooperation with the fluid transfer structure, once the substrate is mounted on the medical support device proper; and
(3) is capable of supplying gas to the diluent-supplying channel, and the fluid channels further provided with (4) a gas-liquid separator placed at a part downstream of the mixing gadget and upstream of the biological component sensor in the biological component-measuring channel.

Yet another embodiment is a biological component-measuring unit according to any one of the above embodiments, where the fluid channels further have a calibrating liquid-supplying channel which
(1) is detachably coupled with a calibrating liquid-drawing channel for drawing a calibrating liquid from a calibrating liquid storage tank;
(2) makes it possible to transfer the calibrating liquid in the calibrating liquid-supplying channel in one direction in cooperation with the fluid transfer structure, once the substrate is mounted on the medical support device proper; and
(3) is capable of supplying the calibrating liquid at a part upstream of the biological component sensor in the biological component-measuring channel.

Yet another embodiment is a biological component-measuring unit as above, wherein
the biological component-measuring channel has a biological component-measuring channel make-and-break part at which fluid flow through the biological component-measuring channel is made or broken by a first fluid channel make-and-break switch with which the medical support device proper is provided once the substrate is attached to the medical support device proper, wherein the biological component-measuring channel make-and-break part is located at a junction where the diluent-supplying channel is connected to the component-measuring channel or a part upstream of the junction;
the diluent-supplying channel has a diluent-supplying channel make-and-break part at which fluid flow through the diluent-supplying channel is made or broken by a second fluid channel make-and-break switch with which the medical support device proper is provided once the substrate is attached to the medical support device proper, wherein the diluent-supplying channel make-and-break part is located at the junction or a part upstream of the junction;
fluid flow through the biological component-measuring channel is broken at the biological component-measuring channel make-and-break part when fluid flow through the diluent-supplying channel is made at the diluent-supplying channel make-and-break part; and
fluid flow through the biological component-measuring channel is made at the biological component-measuring channel make-and-break part when fluid flow through the diluent-supplying channel is broken at the diluent-supplying channel make-and-break part.

A further embodiment is a package of a biological component-measuring unit made by packing the biological component-measuring unit according to any one of the first to seventh means, with a packing material in an isolated and sterile condition.

Another embodiment is a medical support instrument kit comprising the biological component-measuring unit and at least one requisite fluid-contacting member other than the biological component-measuring unit and the medical support device proper, both arranged in the kit.

A further aspect of the embodiment includes a package of a medical support instrument kit made by packing the medical support instrument kit, with a packing material in an isolated and sterile condition.

The biological component-measuring unit according to the present invention has a substrate that has been equipped with fluid channels, which enable the operator to make a medical support device, such as an artificial endocrine pancreas device proper, ready for use just by attaching the substrate to the device proper. The unit of the present invention eliminates connecting fluid channels one by one. As a result, the unit is capable of reducing the amount of work associated with connecting fluid channels when a biological component-measuring unit, such as a unit for measuring blood sugar levels, is attached to a medical support device such as an artificial endocrine pancreas device proper, which leads to an improvement of workability. The reduction of work associated with connecting fluid channels also decreases the amount of work in an unhygienic condition caused by dirt of the fluid channels. Therefore the present invention provides a biological component-measuring unit, with which workability can be improved and which enables the clinical examiner to measure biological components such as blood sugar levels by a hygienic operation.

In addition, a fluid in each fluid channel can be discharged from the channel fixed to the substrate of the used biological component-measuring unit, after the completion of the measurement of biological components such as glucose, which enables the operator to discard the unit such as a blood sugar level-measuring unit just by detaching the substrate from a medical support device proper such as an artificial endocrine pancreas device proper. The unit eliminates disconnecting fluid channels of a biological component-measuring unit such as a blood sugar level-measuring unit after its use, and prevents the operator from contact things like body fluids adhering to unit parts such as fluid channels. Also from this viewpoint, a biological component-measuring unit provided by the present invention is capable of improving workability, and enables the clinical examiner to measure biological components such as blood sugar levels by a hygienic operation.

Furthermore, because a biological component-measuring unit is kept sterile in the package of a biological component-measuring unit, the clinical examiner is capable of operating a medical support device just by taking the biological component-measuring unit out of the package and attaching it to the medical support device proper. Also, after the operation of the medical support device, the used biological component-measuring unit may be detached from the device proper and discarded. Therefore the present invention provides a safe package of a biological component-measuring unit whose operability is excellent, which is hygienic, and which gives the operator fewer opportunities to contact patients' body fluids.

Moreover, members and parts that are necessary to operate a medical support device and that directly contact body fluids and/or liquids essential for medical support are arranged on a substrate. Therefore, employing the substrate, the present invention provides a medical support instrument kit, which enables the operator to make a medical support device, such as an artificial endocrine pancreas device, ready for operation with an improved efficiency and workability only by taking necessary fluid-contacting parts and members from the substrate and attaching them to the medical support device proper.

The present invention also provides a package of a medical support instrument kit, which enables the clinical examiner to make a medical support device ready for operation hygienically and with high operability.

DETAILED DESCRIPTION OF THE INVENTION

Figure 1:
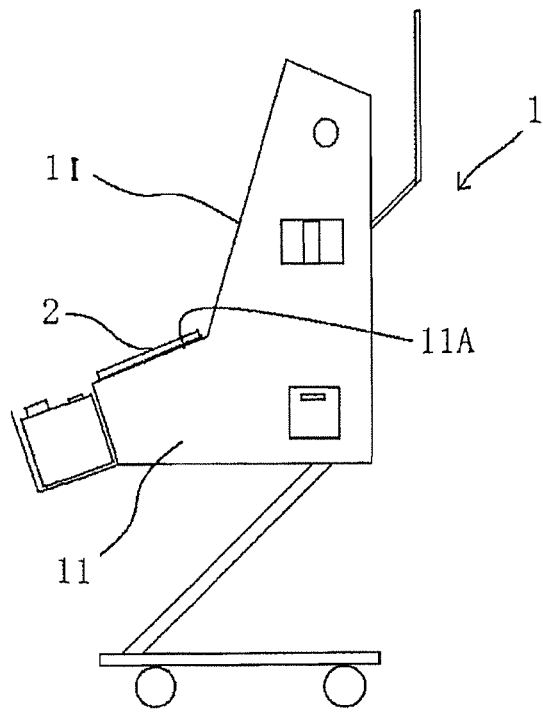
FIG. 1 is a schematic illustration showing an artificial endocrine pancreas device proper to which a blood sugar level-measuring unit is attached.

A biological component-measuring unit is so formed that it is capable of measuring biological components, whose measurement is necessary for medical practice, and it enables the operator to make a medical support device ready for operation efficiently and hygienically.

The biological components, the qualitative or quantitative analysis of which is necessary for medical practice, may include glucose, urea, uric acid, lactose, sucrose, lactate, ethanol, glutamic acid, ammonia, creatinine, and oxygen. Medical practice may sometimes require measurement of other properties, such as the pH value and the oxygen concentration, of body fluids. In the context of the present invention, the term "biological components" includes properties such as the pH value and the oxygen concentration.

A medical support device is a device necessary for medical doctors and veterinarians to understand the condition of a living thing accurately. Examples of medical support devices include artificial endocrine pancreas devices for supplying insulin to living things, dialyzers for dialyzing, urea concentration meters for measuring the urea content included in the body fluids of a living thing, uric acid concentration meters for measuring a uric-acid content in the body fluids of a living thing, sugar concentration meters for measuring sugar such as lactose and sucrose in the body fluids of a living thing, lactic acid concentration meters for measuring lactic acids such as lactate, glutamic acid concentration meters for measuring the glutamic acid content in the body fluids of a living thing, ammonia concentration meters for measuring an ammonia content in the body fluids of a living thing, and creatinine concentration meters for measuring a creatinine content in the body fluids of a living thing.

These various medical support devices are necessary to take exact medical action. The present invention relates to a biological component-measuring unit by which the clinical examiner is able to make a medical support device ready for operation efficiently and hygienically. For the biological component sensor, included in the unit, to measure a biological component may be employed various sensors depending on the kinds of biological components to be measured.

Examples of such biological component sensors, which may sometimes be called "biosensors" hereinafter, include enzyme sensors utilizing enzymes, microorganism sensors employing microorganisms, and hybrid sensors utilizing enzymes and microorganisms.

The enzyme or microorganism immobilized in such a biosensor is selected depending on the target to be measured, or the biological component. For example, when the target to be measured is glucose, β-D-glucose oxidase or *Pseudomonas fluorecens* may be employed as biosensor. When the target is urea, urease may be employed as biosensor; when the target is uric acid, uricase may be employed; for lactate may be used lactate oxidase; for lactose may be employed lactase or β-galactosidase; for ethanol may be employed alcohol oxidase or *Trichosporon brassicaes*; for glutamic acid may be employed glutamate dehydrogenase or *Escherichia coli*; and for ammonia may be employed nitrifying bacteria.

The biological component measuring-unit according to the present invention is capable of dealing with one or more measurable biological components. When two or more biological components are measured, the unit should be equipped with two or more biosensors in the biological component-measuring channel. Another way to measure several components may be to make the biological component-measuring channel branch off and to provide each branch channel with one or more biosensors.

Attaching the biological component-measuring unit to a medical support device proper makes the device ready for operation.

The substrate of the biological component-measuring unit is fixedly provided with fluid channels capable of forcibly or actively transferring body fluids in one direction and at a constant flow rate in cooperation with the fluid transfer structure fixed to the medical support device proper. The fluids flowing in the fluid channels may include body fluids sampled from a living thing, such as blood, urine, lymph and cerebrospinal fluid, mixtures of such body fluids and other liquids such as physiological saline or diluents, calibrating liquids for calibrating the biosensors, and waste liquids discharged after the measurement. In this specification we sometimes call these various fluids, mixtures and liquids "fluids" in general. However, a person skilled in the art to which the present invention belongs will easily understand which fluid, mixture or liquid is meant by a general term "fluid" in the context.

On the substrate of the biological component-measuring unit may be arranged at predetermined locations, in addition to the fluid channels, fluid-contacting members and parts, which members and parts are not mounted on the medical support device proper but necessary to operate the medical support device. The medical support instrument kit according to the present invention is made by arranging these members and parts as well as the fluid channels on the substrate.

Examples of the members and parts that directly contact fluids may include an indwelling needle, a catheter, a physiological saline storage tank, a physiological saline-drawing pipe for drawing physiological saline from the tank, an inlet for introducing the physiological saline drawn through the physiological saline-drawing pipe to a catheter, a diluent storage tank in which various diluents, such as buffer solutions, which are added when necessary, are stored, diluent-drawing pipes for drawing a diluent from the diluent storage tank, diluent-supplying channels for sending the diluent to the fluid transfer structure, a calibrating liquid storage tank in which a calibrating liquid for calibrating the biosensors is stored, a calibrating liquid-drawing pipe for drawing the calibrating liquid from the calibrating liquid storage tank, a calibrating liquid-transferring channel for sending the calibrating liquid to the fluid transfer structure, a waste liquid storage tank in which waste liquid discharged from the biosensors is stored, and other members and instruments that may contact fluids. In summary, the fluid-contacting members and parts include all such members that are not part of the medical support device proper but necessary to make the medical support device ready for operation once the biological component-measuring unit with those fluid-contacting members is attached to the medical support device proper.

The invention is described in more detail through the description of an exemplary embodiment. A glucose-measuring unit is described as a non-limiting example of a biological component-measuring unit, and an instrument kit for an artificial endocrine pancreas device is described as a non-limiting example of the instrument kit for a medical support device, which instrument kit is equipped with the fluid-contacting members and parts that are not mounted on the medical support device proper but necessary to the biological component-measuring unit and further to the medical support device.

As shown in FIG. 1, a blood sugar level-measuring unit 2, which is an example of the biological component-measuring unit according to the present invention, is attached to an artificial endocrine pancreas device proper 1, which is an example of the medical support device proper. The artificial endocrine pancreas device proper 1 has a front portion 1I for operation of the device, and a mount table 11 that horizontally projects from the front portion 1I toward the operator.

The mount table 11 can be positioned so that the operator can comfortably operate it with his/her hands without bending himself/herself when s/he stands in front of the device proper. When the operator operates it in a standing posture, the mount table 11 should preferably have a mounting face 11A that is inclined upward from the operator to the front portion 11 of the artificial endocrine pancreas device. Although there is no limitation on the shape of the mounting face 11A, this embodiment employs a rectangular shape for it. The angle θ at which the mounting face 11A is inclined, or the angle θ made by a virtual horizontal line extending horizontally from the front portion 1I and the mounting face 11A sloping up from the lower end horizontal line thereof should be from not less than 60 degrees to not more than 80 degrees. When the mounting face 11A is inclined at an inclination angle within the range specified above, gas bubbles in various fluid channels fixed to the substrate that will be attached to the mounting face 11A can be moved upward, which makes it possible to separate gas from the fluids. This inclination also provides the operator with a good view of the substrate and good operability. For smooth operation by operators with different heights, the mount table 11 may be designed so as to move upward and downward with a device such as a lifting gear, whereby the blood sugar level-measuring unit 2 can be set vertically at a level of each operator's eyes or a location that enables each operator to operate the device with his/her hands smoothly.

The mount table 11 is provided with a fluid transfer structure, which is described hereinafter, and fluid channel make-and-break switches such as a first flow path changeover switch and a second flow path changeover switch.

Figure 5:
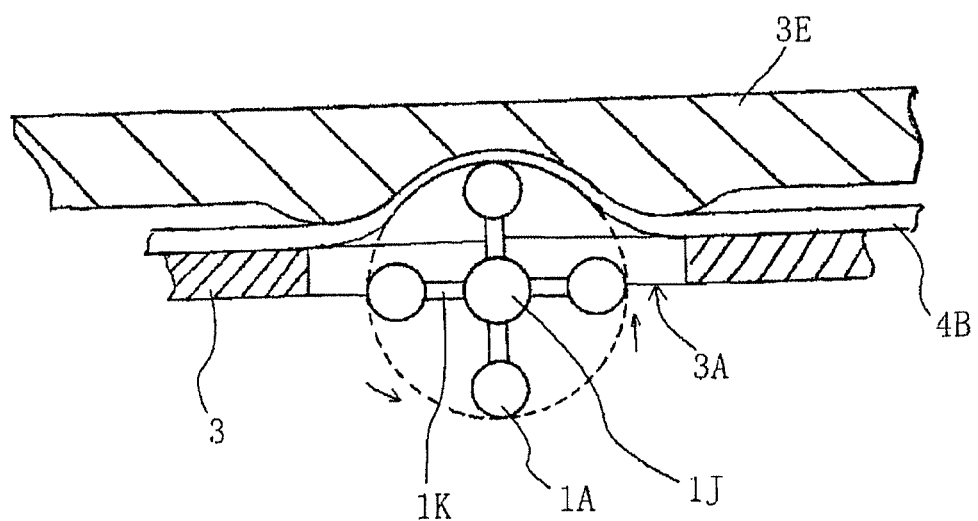
FIG. 5 is a schematic illustration showing the sectional structure of a part around the window for rollers of the blood sugar level-measuring unit according to the present invention.

The fluid transfer structure of the present invention may include various structures, as long as it has a mechanical structure capable of transferring fluids in the fluid channels in one direction in cooperation with the fluid channels of the blood sugar level-measuring unit 2. Furthermore, the fluid transfer structure may take various mechanical structures, as long as it is provided with various mechanical structures with the function capable of making and breaking fluid flow in the fluid channels in cooperation with various fluid channels such as the glucose-measuring channel in the blood sugar level-measuring unit 2. One example of the fluid transfer structure that works in cooperation with the blood sugar level-measuring unit 2 in this embodiment is such that the means has a structure capable of exerting physical actions to the fluids, which actions transfer fluids such as blood, a diluent such as a buffer, and waste liquid to predetermined parts. A specific example is, as shown in FIG. 5, a squeezing roller comprising rollers 1A for squeezing elastic and flexible pipes, such as a pipe for a blood transferring channel 4B, sticks 1K for supporting these rollers 1A, a rotor 1J for supporting the sticks 1A connected thereto, and a holding plate 3E, which squeezing roller provides the channel with squeezing actions. The rotor 1J of this squeezing roller rotates around the axis thereof, which, in turn, rotates the rollers 1A around the rotor 1J. A device comprising a flexible pipe, and a combination of rollers 1A, sticks 1K, a rotor 1J and a holding plate 3E is called roller pump.

Other examples of the fluid transfer structure whose structures are similar to that with the squeezing function shown in FIG. 5 are a device with a structure of the linear peristaltic pump except the tube for transferring fluid, and a device with a structure of the rotary peristaltic pump except the tube for transferring fluid. Another specific example, other than those with the squeezing function, may be a fluid transfer structure with a pressing function illustrated in FIG. 10.

Figure 10:
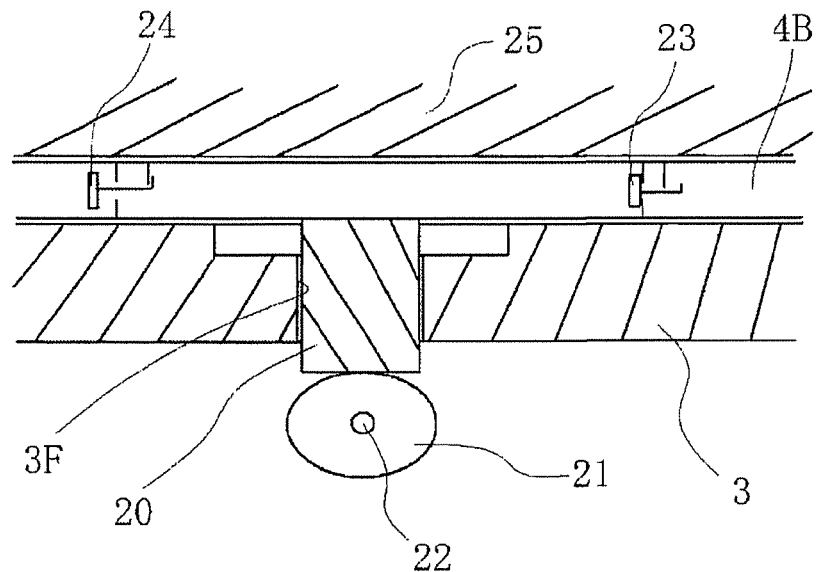
FIG. 10 is an illustration showing another example of the fluid transfer structure.

The fluid transfer structure with a pressing function comprises, as shown in FIG. 10, a pressing member 20 capable of projecting from and sinking under the upper face of the substrate 3 of the blood sugar level-measuring device 2 through a hole 3F pierced in the substrate, and an eccentric rotating cam 21 capable of rotating with keeping one end of the pressing member 20 contacted. When the eccentric rotating cam 21 rotates around its rotating shaft 22, the pressing member 20 translates the rotation into such a vertical movement that the member projects from the upper face of the substrate and sinks under it repeatedly through the hole 3F. On the other hand, each of the fluid channels, such as a blood-transferring channel 4B, is provided with a first poppet valve 23 and a second poppet valve 24 inside the channel, as described hereinafter. Reference numeral 25 denotes a holding plate to hold the fluid channel. The compression of the channel by the pressing member 20 makes smaller the volume of the space inside the channel delimited by the first poppet valve 23 and the second poppet valve 24. As a result, the first poppet valve 23 is closed while the second poppet valve 24 is opened, which makes the fluid in the delimited space flow out through the second poppet valve 24. The pressing member 20 starts retracting after the volume reaches the minimum. When the volume returns to its maximum, the first poppet valve 23 becomes opened while the second poppet valve 24 becomes closed, which invites an inflow of the fluid into the delimited space through the first poppet valve 23. Through the repetition of this vertical movement, or the upward-and-downward movement of the pressing member, the inflow of the fluid into the delimited space and the outflow thereof from the space are repeated alternately and the fluid is forcibly or positively transferred through the fluid channel Since the fluid transfer structure shown in FIG. 10, in cooperation with the fluid channel, makes the fluid flow into and out of the delimited space repeatedly, it can be said that the fluid transfer structure and the fluid channel provided with valves such as the poppet valves make sort of a pump.

Therefore a mechanism providing a pumping function in cooperation with a fluid channel may also be included in the fluid transfer structure of the present invention, fixed to the mount table of the artificial endocrine pancreas device proper.

For the fluid transfer structure of the artificial endocrine pancreas device proper 1, which is an embodiment of the present invention, is employed a multiple roller device having a single rotating shaft, and several elongated rollers supported by the shaft with their axes parallel to the axis of the rotating shaft. The fluids in all the fluid channels through which the fluids must be transferred are transferred by the squeezing action of the elongated rollers. The flow rate of the fluid transferred in the fluid channel per unit time period is decided by the unit sectional area of a fluid channel. In other words, the flow rate of the fluid transferred through the squeezing by the multiple roller device may be adjusted by appropriately adjusting the inner diameter of the fluid channel.

Figure 3:
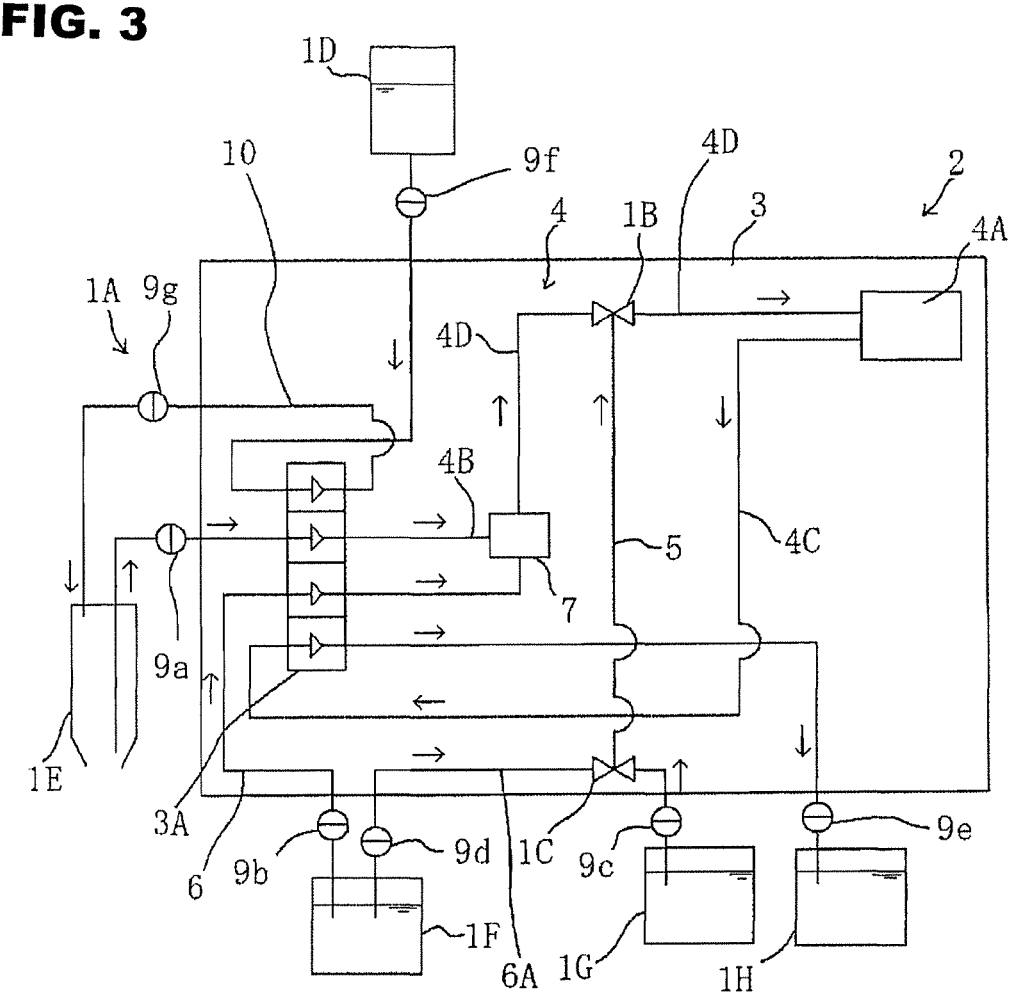
FIG. 3 is a block diagram showing an example of a blood sugar level-measuring unit according to an embodiment of the present invention.

As shown in FIG. 3, the blood sugar level-measuring unit 2, which is an embodiment of the present invention, is provided with a substrate 3, a glucose-measuring channel 4, which is an example of the fluid channels and the biological component-measuring channel, a calibrating liquid-supplying channel 5, which is another example of the fluid channels, a diluent-supplying channel 6, which is still another example of the fluid channels, and a mixing gadget 7.

There is no special limitation on the material of the substrate 3, as long as those various fluids can be fixed to the substrate. In this embodiment is employed a hard synthetic resin. Soft and flexible synthetic resins may be used depending on the situations. Specific examples of the material for the substrate 3 are a sheet made of PVC, a hard film of hard PVC or PET, and a soft PVC to which PVC tubes are easily stuck. Although the substrate 3 may be produced by machining a raw material plate, the production by molding is preferable from the viewpoint of the price of the material, a reduction of waste material such as chips from the machining, and easiness of the mass production. For the molding, a method suitable for production in a medium or large quantity, such as compression molding or injection molding, may be used. The tubes may be fixed to the substrate by sticking them to predetermined locations on the substrate. Another method may be a die slide injection, often abbreviated to DSI, which is a precision molding by which the hollow tubes and the substrate are integrally molded. The DSI method does not require the sticking of the tubes after arranging them on the substrate. Still another method that may be utilized is fusible core injection molding in which tubes, each with a core inside it, are molded and the cores are melted away, whereby hollow tubes are prepared. The substrate 3 should preferably be made of an elastic soft material so that the substrate will have a certain dimensional tolerance.

Figure 2:
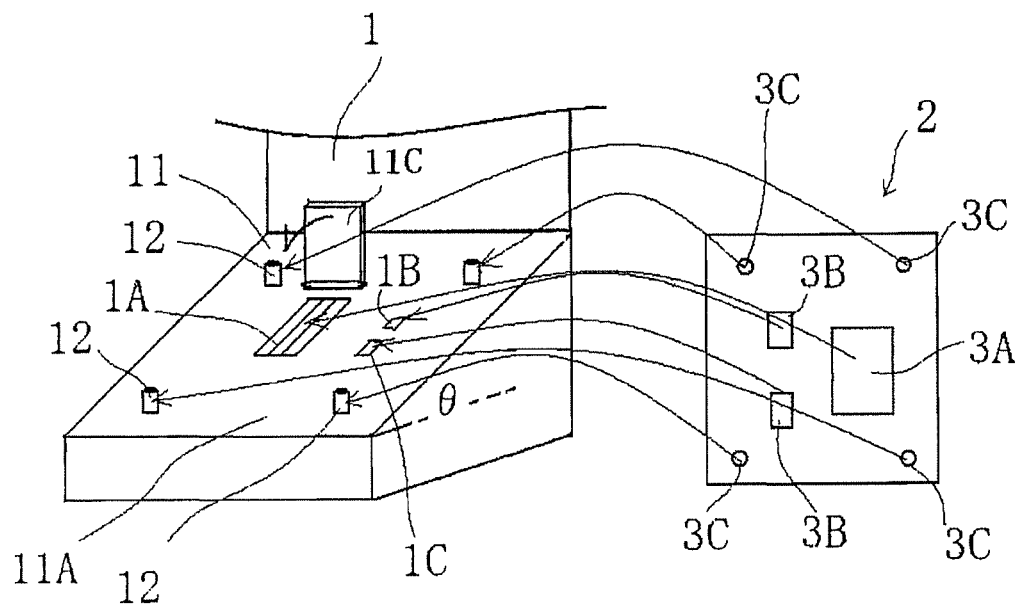
FIG. 2 is a schematic illustration showing a mount table of an artificial endocrine pancreas device proper and a blood sugar level-measuring unit.

As shown in FIG. 2, the substrate 3 has holes for attaching it in an appropriate location. The holes respectively receive attaching pins 12, projecting from parts around the four corners of the mounting face 11A. By inserting the attaching pins 12 into the holes, the operator can easily attach the blood sugar level-measuring unit 2 to the mount table 11. The operability of this blood sugar level-measuring unit is improved also in this respect.

These attaching pins 12 are protrusions projecting from predetermined parts of the surface of the mount table 11. Design modifications may be made to the mechanism for attaching the substrate to the mount table.

As an example of a design modification, two attaching rods 3D are respectively fixed to first and second edges of the substrate 3. The first edge corresponds to the upper edge and the second edge to the lower edge when this substrate 3 is attached to the mount table 11. The substrate 3 may be detachably attached to the mount table 11 by making the attaching rods 3D abut on the attaching pins 12. In order to fix the attaching rods 3D to the substrate 3, each of the upper and lower edges are incurvated so as to form a hollow cylinder, into which each attaching rod 3D is inserted.

Figure 18:
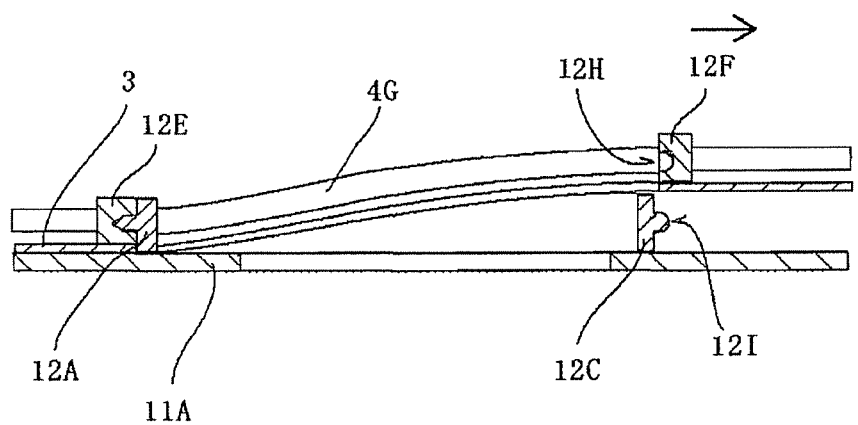
FIG. 18 is a sectional view showing the state in which the tube holders that have not been engaged yet are being drawn up to a second pair of attaching pins, which have not been engaged yet, either, and the holders are about to be engaged with the second pair of attaching pins, which follows the state shown in FIG. 17.
Figure 19:
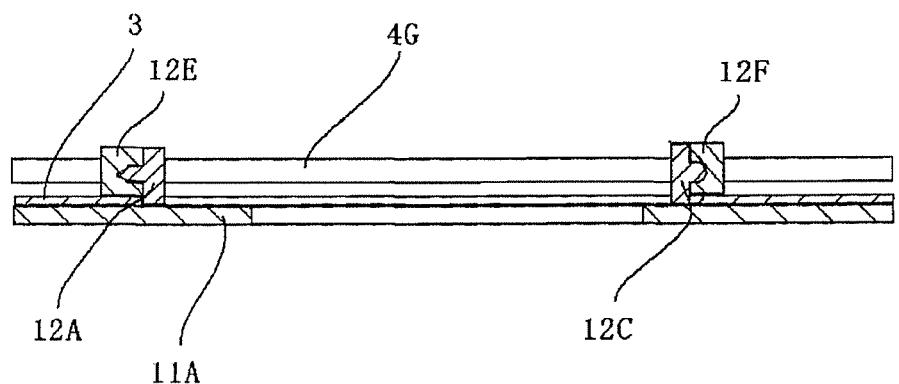
FIG. 19 is a sectional view showing the state in which the tube holders are completely engaged with the attaching pins.
Figure 20:
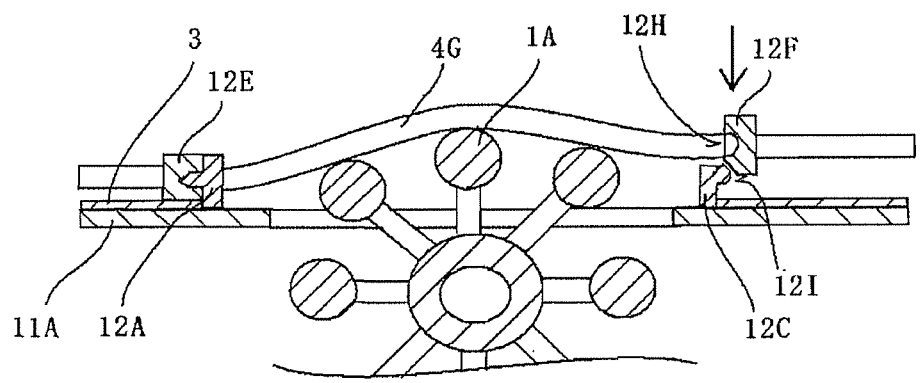
FIG. 20 is a sectional view showing the same state as that in FIG. 18, except that part of the shape of the attaching pins and part of the shape of the tube holders are different from those in FIG. 18 and the figure includes part of the rollers.

Another design modification is the device shown in FIGS. 14-19. The tubes 4G running across a window 3A of the substrate 3 are provided with a tube holder 12E at a part upstream of the window 3A and another tube holder 12F at a part down stream thereof. The tube holders 12E, 12F are secured to the tubes 4G by appropriate means such as sticking, and both or one of the tube holders is also secured to the substrate 3. Notches or recesses are formed in each of the tube holders 12E, 12F respectively at such a location in proximity to one end thereof and such another location in proximity of the other end thereof that the notches or recesses formed in one tube holder respectively face the ones formed in the other tube holder. The recesses in the tube holders 12E and 12F are named engaging recesses 12G and 12H respectively. The shapes of the engaging recesses 12G, 12H can be complementary to the shapes of the projections of the attaching pins so that each projection will be tightly engaged with its paired engaging recess. On the mount table 11 onto which the substrate 3 are attached are arranged attaching pins with projections at such locations that engaging recesses 12G, 12H should be engaged with projections of those attaching pins 12A, 12B, 12C, 12D. The distance between the attaching pins should be adjusted that the tube will not hang slack and the substrate 3 is settled by the two tube holders once the projections of the attaching pins engage with the engaging recesses 12G, 12H. The projections of the attaching pins are located at the side where the first engagement is carried out, or those of the attaching pins 12A, 12B in FIG. 14, each may have such a shape that the projection tightly engages with the engaging recess of the tube holder 12E. One example of the shape is a slightly elongated cylinder with a pointing tip. The projections of the attaching pins 12C, 12D, located at the side where the following engagement is carried out, each may have such a shape as to enable the operator to draw the second engaging recesses 12H of the tube holder 12F over the second set of attaching pins, and to set the projections into the recesses by holding the tube holder down to the attaching pins. Examples of the shape may include a relatively short cylinder with a round tip, and a general hemisphere. The combination of the tube holders 12E, 12F and the projections of the attaching pins 12A, 12B, 12C, 12D makes it possible to easily attach the substrate 3 to or detach it from the mount table 11. This combination is advantageous, especially because the tubes and/or the substrate hardly slip off even when the tubes are squeezed by the rollers 1A. Also, FIG. 20 is a sectional view showing another embodiment in the same state as that in FIG. 18, except that the shape of the tube holder 12F and that of the projection 12C are different from those in FIG. 18. FIG. 20 includes part of the rollers 1A, which functions as a rotary peristaltic pump, and the figure also shows the shape of a tube 4G under the squeezing force. In the embodiment shown in FIG. 20, the lower corner of the tube holder, which corner contacts the attaching pin 120, is cut off. This cut-off enables the operator to easily engage the engaging recess 12H of the tube holder 12F with the projection I of the attaching pin 12C just by pushing the tube holder downward. The tension of the tube 4G prevents the tube holder 12F from disengaging easily. To enhance difficulty of the disengagement of the tube holder 12F, the rollers LA should be rotated clockwise. If the substrate 3 is covered with a lid 11C for the opening in the mounting face 11A after the substrate 3 is attached to the mounting face 11A, the tubes 4G and the tube holders 12E, 12F are held down by the lid 11C. This holding-down ensures that the tubes 4G and the tube holders 12E, 12F can be secured so firmly onto the mounting face 11A that they will not be disconnected from the mounting face 11A even though the tubes 4G may be stretched a little by the squeezing of the rollers 1A.

Figure 14:
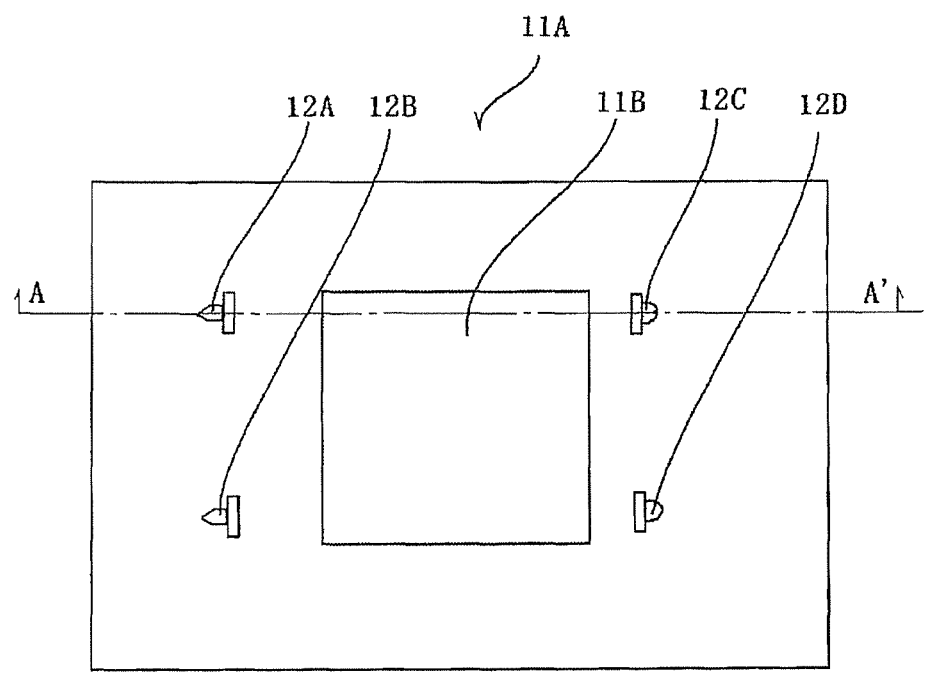
FIG. 14 is a plan view showing apart of the mount table around the opening for rollers, of an artificial endocrine pancreas device proper.
Figure 15:
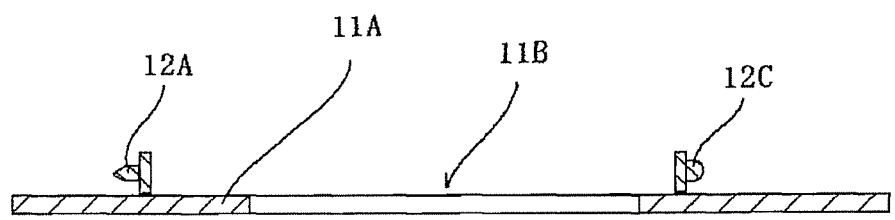
FIG. 15 is a sectional view taken along line A-A' in FIG. 14.
Figure 16:
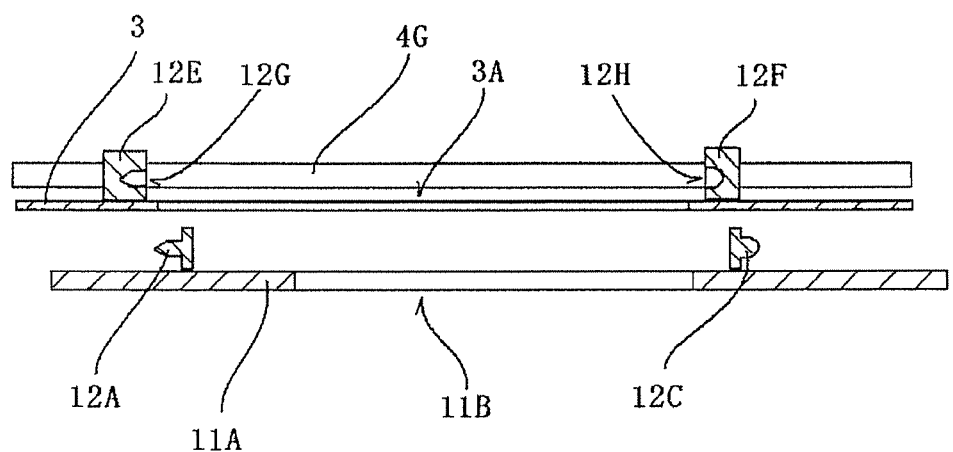
FIG. 16 is a sectional view, shown in the same way as in FIG. 15, illustrating the part of the mount table around the opening for rollers, of the artificial endocrine pancreas device proper over which the substrate to be attached to the mount table is placed.
Figure 17:
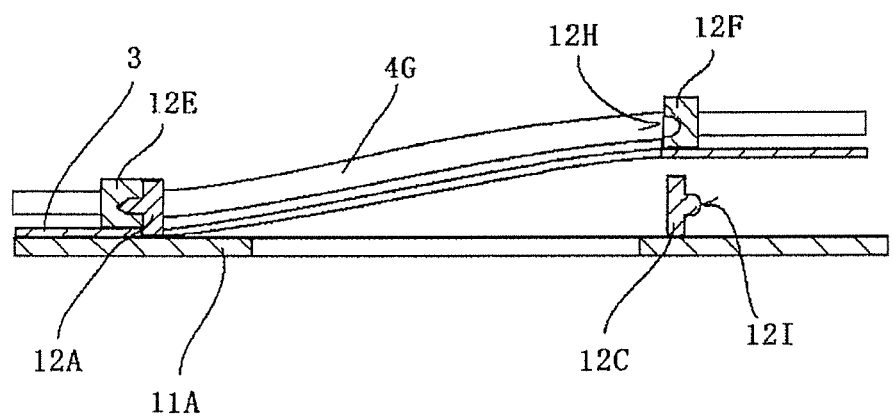
FIG. 17 is a sectional view showing the state in which the tube holders at one side are engaged with a first pair of attaching pins, which follows the state shown in FIG. 16.

A specific example of how to attach the substrate to the mounting face is described below. As shown in FIG. 14, four attaching pins 12A, 12B, 12C, 12D have been arranged on the mounting face 11A of the mount table 11, around the opening 11 in which the rollers 1A are placed. In FIGS. 14-19, the rollers are not shown. The distance between the attaching pins, parallel to the running of the tubes, is such that the tube holders do not disengage from the attaching pins due to the tension of the tube when the respective projections of the four attaching pins are engaged with the engaging recesses 12G, 12H of the tube holders 12E, 12F respectively located upstream to and downstream to the window 3A of the substrate 3, across which the tubes 4G secured to the substrate run. FIG. 15 is a sectional view taken along line A-A' in FIG. 12. FIG. 16 is a fragmentary section illustrating a part of the mounting face shown in FIG. 15, the part being around the opening for the rollers over which the substrate 3 is placed. FIG. 17 is a sectional view illustrating the state in which the tube holder 12E is engaged with the attaching pins 12A, 12B. FIG. 18 is a sectional view showing the state in which the tube holder 12F is being drawn in the right direction in the figure, up to the projection 121 of the attaching pin 12C. Pushing the tube holder 12F downward in this state will make the tube holder engage with the attaching pins 12C, 12D. FIG. 19 illustrates the state in which the tube holder 12F is completely engaged with the attaching pin 12C and the substrate 3 is firmly set on the mounting face 11A.

Figure 21:
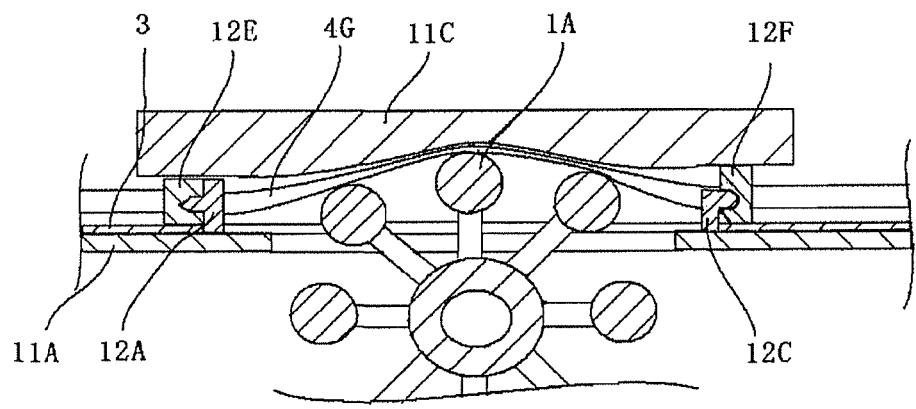
FIG. 21 is a sectional view showing the state in which the tube holders are completely engaged with the attaching pins and the opening is covered with a lid with which the mount table is provided, which state follows the state shown in FIG. 20.

In the embodiment shown in FIG. 2, the substrate 3 has a window for the rollers 3A and two apertures 3B. The location of the window for the rollers 3A is so decided that the various fluid channels so disposed as to run across the window 3A will be squeezed by the rollers mounted on the mount table 11. The respective locations of the two apertures 3B are so decided that the protrusions of a first flow path changeover switch 1B and those of a second flow path changeover switch 1C will stick out from the mount table 11 through the respective apertures. The window for the rollers 3A of the substrate 3, after the substrate 3 is attached to the mount table, is held down by a lid for the opening 11C with which the mounting face 11A of the mount table 11 is provided. The lid for the opening 11C serves as the holding plate 3E. FIG. 21 is a sectional view showing the state in which the tube holders 12E, 12F are completely engaged with the attaching pins 12A, 12B, 12C, 12D disposed on the mounting face 11A and the lid for the opening 11C disposed on the mounting face 11A is laid on them. This structure, comprised of the tubes sandwiched and squeezed between the rollers 1A and the lid for the opening 11C, serves as a rotary peristaltic pump.

This embodiment, which employs the window for the rollers 3A formed in the substrate 3, enables each roller of the multiple roller to directly contact the fluid channels such as a glucose-measuring channel and to squeeze the channels. However, as long as fluids in the fluid channels are transferred by the fluid transfer structure, it is not necessary to form such a window as the window for the rollers 3A in the substrate. When the substrate is made of a flexible thin sheet, the fluid channels may be squeezed by the rollers with this substrate that does not have the window 3A in between. The latter embodiment is advantageous when the tubes are broken, because the substrate made of a thin sheet serves as a cover with which the mount table is overlaid, and the fluids flowing out of the tubes are prevented from coming into the medical support device proper 1.

The substrate 3 is equipped with a glucose-measuring channel 4, a calibrating liquid-supplying channel 5, a diluent-supplying channel 6, and a mixing gadget 7.

As shown in FIG. 3, the glucose-measuring channel 4 is in the shape of a tube made of, for example a flexible material, so that sampled blood is transferred through the channel 4 by, for example, the rollers 1A of the fluid transfer structure to a glucose sensor 4A, which is an example of the biological component sensor. In this embodiment, the glucose-measuring channel 4 is further provided with a blood-transferring channel 4B for transferring sampled blood to a mixer 7, which is an example of the mixing gadget, a sample liquid-transferring channel 4D for transferring a blood-containing sample, a mixture of the sampled blood and a diluent made by the mixer 7, and a waste liquid-transferring channel 4C for transferring a fluid the measurement of which has been completed in the glucose sensor 4A as waste liquid.

Figure 11:
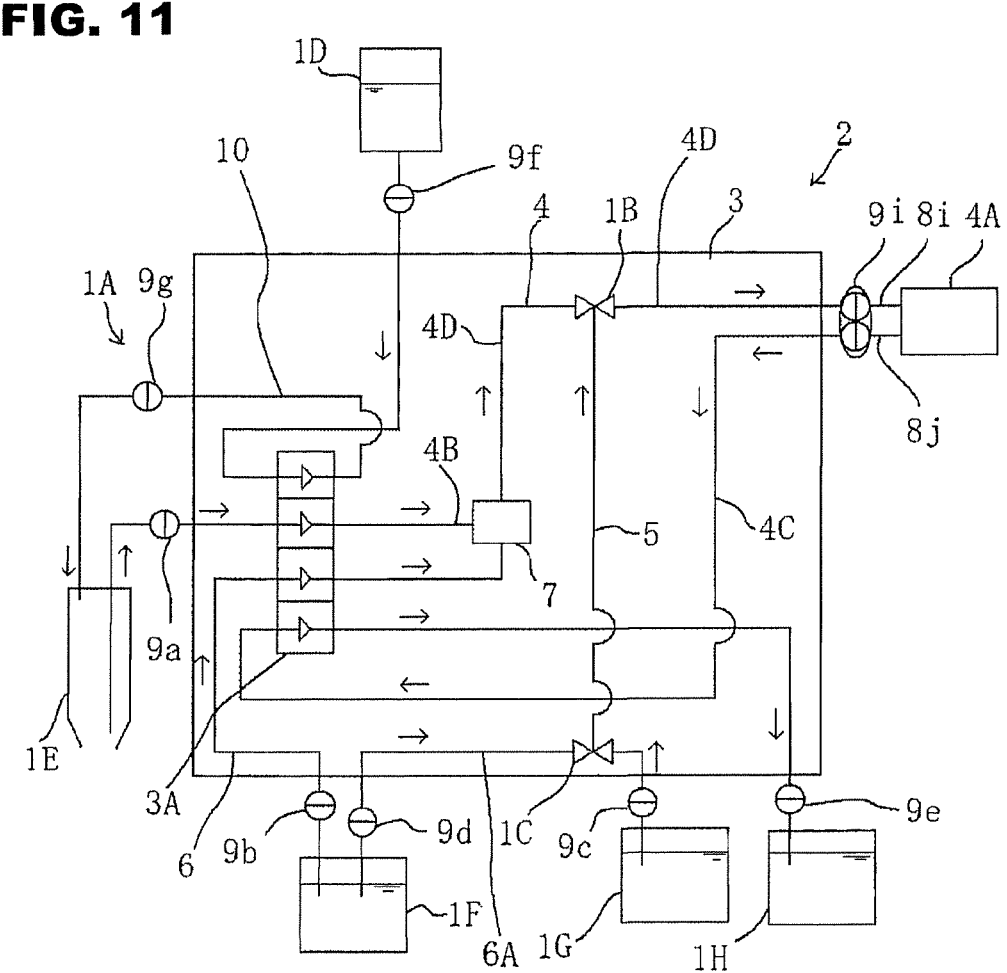
FIG. 11 is a block diagram illustrating an example of the blood sugar level-measuring unit according to an embodiment of the present invention.

In another embodiment shown in FIG. 11, the glucose sensor 4A shown in FIG. 3 is not placed in the glucose-measuring channel 4 on the substrate 3. At the location where the glucose sensor 4A is placed in FIG. 3 are disposed two connectors 9i that are respectively connected to a sample inlet 8i of a glucose sensor 4A provided outside the blood sugar level-measuring unit 2 and a sample outlet 8j thereof. The other elements are the same as those in the embodiment shown in FIG. 3. The connectors 9i should connect the sample liquid-transferring channel 4D with the sample inlet 8i of the glucose sensor and the waste liquid-transferring channel 4C with the sample outlet 8j thereof. The two connectors may be, for example, integrated into one structure that provides two independent connections, or made separately. The connections of the fluid channels provided by the connectors should be free from leakage. Specifically, the connector 9i receiving the transferring channels, and the connector 9i receiving the sample inlet 8i and the sample outlet 8j should be contact bonded, or tightly joined with connecting elements such as bolts and nuts. From the viewpoint of operability of the blood sugar level-measuring unit 2 in practical use, the most preferable are connectors that can be attached or detached very easily just by applying a pressure by the hand. The advantageous characteristic of this embodiment lies in easily providing other measurements, such as a measurement of a pH value or a measurement of a lactic acid level, just by exchanging the glucose sensor 4A with other sensors. Also, when sensors such as a glucose sensor 4A are expensive, the operator does not have to use the sensors only once and throw them away; s/he can throw away only the blood sugar level-measuring unit 2 of this embodiment.

To one end of the blood-transferring channel 4B is attached a connector 9a that is so designed as to be detachably connected to the end of a blood-drawing channel, such as a blood sampling channel, of a blood sampling device such as a catheter. The one end of the blood-transferring channel 4B provided with the connector 9a is outside the substrate 3. Portions of the blood-transferring channel 4B other than the one end are neatly arranged on the surface of the substrate 3 together with other fluid channels, and a central portion of the channel 4B is so disposed that the portion runs across the window for the rollers 3A with tension. This embodiment employs a double lumen catheter for the catheter 1E.

As shown in FIG. 3, the sample liquid-transferring channel 4D is neatly arranged with other fluid channels on the surface of the substrate 3. A part of the sample liquid-transferring channel 4D, which is between the two ends of the channel, is disposed so that the part extends across the aperture 3B with tension, in order to be provided with the first flow path changeover switch 1B.

For the glucose sensor 4A that is connected to the glucose-measuring channel 4 may employ, for example, a biosensor made by coating a carbon electrode with an osmium polymer, drying the coated electrode at room temperature, applying an enzyme solution thereto to make a film, and immobilizing the enzyme by a cross-linking agent such as glutaraldehyde. When this biosensor is used as the glucose sensor 4A, an oxidation reaction takes place between peroxide and a peroxidase enzyme, which is immobilized in the osmium polymer, and the reaction is followed by a reduction reaction between the osmium polymer, the peroxidase and the electrode. The electrode potential during these reactions is 0 mV compared with the electrode potential of the silver-silver chloride electrode. Therefore the utilization of the glucose oxidase for the enzyme for the oxidation reaction leads to a quick detection of glucose and an easy measurement of the concentration thereof. The glucose sensor 4A may include, other than that explained above, a glucose sensor including an osmium (II)-bipyridine complex, one including a ruthenium complex, and a glucose sensor with an electrode modified with a polypyrrole into which a tris-osmium complex is immobilized.

Among these various glucose sensors, the biosensor employing the osmium polymer is preferable. Suitable glucose sensors are film sensors having a work electrode of platinum, silver or carbon, and an enzyme film of an osmium polymer impregnated with peroxidase.

The waste liquid-transferring channel 4C is further disposed on the substrate 3. Through the waste liquid-transferring channel 4C the fluid that has been measured by the glucose sensor is discharged as a waste liquid to a waste liquid tank 1H. To one end of this waste liquid-transferring channel 4C is fixed a connector 9e that is so designed that it is capable of being detachably coupled with a connector of the inlet for discharging the waste liquid into the waste liquid tank 1H. The one end of the waste liquid-transferring channel 4C equipped with the connector 9e is outside the substrate 3. Portions of the waste liquid-transferring channel 4C other than the one end are neatly arranged on the surface of the substrate 3 together with other fluid channels. A part of the waste liquid-transferring channel 4C, which part is between the two ends of the channel, is so disposed that the part extends across the window for the rollers 3A.

As shown in FIG. 3, the mixer 7 is connected to a diluent-supplying channel 6 which supplies a diluent stored in a diluent tank 1F, the tank is an example of the diluent storage tank mounted on, for example, an artificial endocrine pancreas device proper, a device other than the blood sugar level-measuring unit 2.

To one end of this diluent-supplying channel 6 is fixed a connector 9b that is so designed that it is capable of being detachably coupled with a connector of a diluent outlet, or a diluent-drawing channel through which the diluent stored in the diluent tank 1F is drawn. The one end of the diluent-supplying channel 6 equipped with the connector 9b is outside the substrate 3. Portions of the diluent-supplying channel 6 other than the one end are neatly arranged on the surface of the substrate 3 together with other fluid channels. A central part of the diluent-supplying channel 6 is so disposed that the part extends across the window for the rollers 3A with tension. The other end, or the end opposite the one end connected to the connector 9b, of the channel is connected with the mixer 7.

The diluent may be any solution as long as it is capable of diluting blood that is transferred through the blood-transferring channel 4B and of keeping constant the pH value of a sample liquid to be introduced into the glucose sensor 4A. An example of the diluent is a phosphoric acid buffer, which is also called a buffer. Therefore the diluent in this embodiment can be considered to be a buffer. When a buffer is used as the diluent, the buffer keeps the pH value of a sample liquid constant, which leads to a stable measurement of a blood sugar level by the glucose sensor that has acute sensitivity to pH values.

As shown in FIG. 3, the first flow path changeover switch 1B is connected to a calibrating liquid-supplying channel 5 which supplies a calibrating liquid stored in a calibrating liquid tank 1G, the tank is an example of the calibrating liquid storage tank mounted on, for example, an artificial endocrine pancreas device proper, a device other than the blood sugar level-measuring unit 2, to the sample liquid-transferring channel 4D. To one end of this calibrating liquid-supplying channel 5 is fixed a connector 9c that is so designed that it is capable of being detachably coupled with a connector of a calibrating liquid outlet, or a calibrating liquid-drawing channel through which the calibrating liquid stored in the calibrating liquid tank 1G is drawn. The one end of the calibrating liquid-supplying channel 5 equipped with the connector 9c is outside the substrate 3. Portions of the calibrating liquid-supplying channel 5 other than the one end are neatly arranged on the surface of the substrate 3 together with other fluid channels. A part of the calibrating liquid-supplying channel 5, which part is between the two ends of the channel, is provided with a second flow path changeover switch 1C.

A second diluent-supplying channel 6A is connected to the second flow path changeover switch 1C. To one end of this second diluent-supplying channel 6A is fixed a connector 9d that is so designed that it is capable of being detachably coupled with a connector of a second diluent outlet through which the diluent, such as a buffer, stored in the diluent tank 1F is drawn. The one end of the second diluent-supplying channel 6A equipped with the connector 9d is outside the substrate 3. Portions of the second diluent-supplying channel 6A other than the one end are neatly arranged on the surface of the substrate 3 together with other fluid channels.

Fixed to the substrate 3 is a physiological saline-transferring channel 10 that sends a physiological saline including heparin, which may sometimes be called just physiological saline hereinafter, stored in a physiological saline tank 1D, mounted on, for example, an artificial endocrine pancreas device proper 1, a device other than the blood sugar level-measuring unit 2, to the catheter 1E.

Fixed to one end of this physiological saline-transferring channel 10 is a connector 9f that is so designed that it is capable of being detachably coupled with a connector of a physiological saline outlet through which the physiological saline stored in the physiological saline tank 1D that is mounted on, for example, an artificial endocrine pancreas device proper 1, a device other than the blood sugar level-measuring unit 2, is drawn. One end of the physiological saline-transferring channel 10 equipped with the connector 9f is outside the substrate 3. On the other hand, fixed to the other end of this physiological saline-transferring channel 10 is a connector 9g so designed that it is capable of being detachably coupled with a connector fixed to an inlet of the catheter 1E. The other end of the physiological saline-transferring channel 10 equipped with the connector 9g is outside the substrate 3. The central part of this physiological saline-transferring channel 10, or part other than the one end and the other end, both being outside of the substrate 3, is neatly arranged on the surface of the substrate 3 together with other fluid channels, and so disposed that a portion of the part runs across the window for the rollers 3A.

The first flow path changeover switch 1B will be explained in detail in the following paragraphs.

Various mechanical structures may be employed for the first flow path changeover switch 1B, as long as they are capable of switching from state (1) in which the blood-transferring channel 4B communicates with the sample liquid-transferring channel 4D to state (2) in which the calibrating liquid-supplying channel 5 communicates with the sample liquid-transferring channel 4D, and switching from state (2) to state (1).

Figure 4:
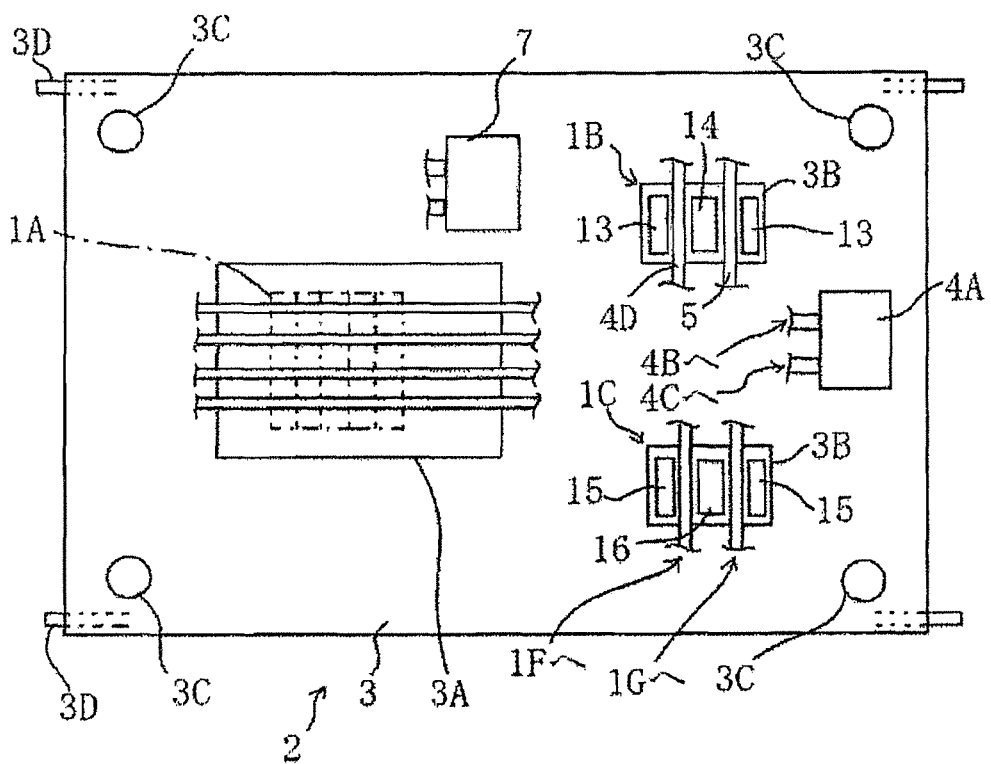
FIG. 4 is a schematic illustration showing a substrate of a blood sugar level-measuring unit according to the present invention.

In an embodiment shown in FIG. 4, a branched tube such as a Y-shaped tube (not shown in the figures), is grafted in the sample liquid-transferring channel 4D; the first and second branches of the Y-shaped tube are interposed in the sample liquid-transferring channel 4D, and the third branch is connected to the calibrating liquid-supplying channel 5. The first flow path changeover switch 1B comprises, as shown in FIG. 4, a pair of first stationary members 13, 13, and a first movable member 14 disposed between the first stationary members and movable toward one first stationary member and the other first stationary member, wherein the pair of first stationary members and the first movable member stick out upward from the surface of the substrate 3 through the aperture 3B formed in the substrate 3 when the blood sugar level-measuring unit 2 is attached to the mount table 11. As understood from FIG. 4, a part of the sample liquid transferring channel 4D, which part is located upstream of the Y-shaped tube, is disposed between one first stationary member 13 and the first movable member 14, and a part of the calibrating liquid-supplying channel 5 is disposed between the other first stationary member 13 and the first movable member 14. When the first movable member 14 moves in such a direction as to hold, for example, the sample liquid transferring channel 4D between the one stationary member 13 and the first movable member to compress it, the sample liquid transferring channel 4D is blocked up, whereby state (2) in which the calibrating liquid-supplying channel 5 communicates with the sample liquid-transferring channel 4D is realized. Alternatively, when the first movable member 14 moves in such a direction as to hold, for example, the calibrating liquid-supplying channel 5 between the other stationary member 13 and the first movable member to compress it, the calibrating liquid-supplying channel 5 is blocked up, whereby state (1) in which the blood-transferring channel 4B communicates with the sample liquid-transferring channel 4D is realized.

As mentioned above, the first flow path changeover switch 1B, which is an example of the fluid channel make-and-break switch, is not limited to the combination of the pair of the first stationary members 13 and the first movable member 14, as long as the switch is capable of changing the ways of the communication. For example, other valves, such as a cross valve, two 2-way valves, or a rotary valve, may be used.

A feature of the present invention is that the make-and-break of fluid channels can be made by the fluid channels arranged on the substrate and the fluid channel make-and-break switch with which the mount table is provided, once the substrate of a biological component-measuring unit, such as a blood sugar level-measuring unit, according to the present invention, is attached to the mount table of a medical support device proper, such as an artificial endocrine pancreas proper. Thus, the blood sugar level-measuring unit 2, which itself does not make or break the fluid channels, obtains the function of making and breaking the fluid channels when the unit is attached to the mount table. As is further below, the second flow path changeover switch 1C provides the same function as the first flow path changeover switch 1B.

The second flow path changeover switch 1C will be explained in detail hereinafter.

Various mechanical structures may be employed for the second flow path changeover switch 1C, as long as they are capable of switching from state (a) in which the second diluent-supplying channel 6A communicates with the calibrating liquid-supplying channel 5 in the section between this second flow path changeover switch 1C and the first flow path changeover switch 1B, to state (b) in which the communication through the calibrating liquid-supplying channel from the calibrating liquid tank 1G to the first flow path changeover switch 1B is established.

In the embodiment shown in FIG. 4, a branched tube such as a Y-shaped tube (not shown in the figures), is grafted in the calibrating liquid-supplying channel 5; the first and second branches of the Y-shaped tube are interposed in the calibrating liquid-supplying channel 5, and the third branch is connected to the second diluent-supplying channel 6A. The second flow path changeover switch 1C comprises, as shown in FIG. 4, a pair of second stationary members 15, 15, and a second movable member 16 disposed between the second stationary members and movable toward one of the second stationary members and the other second stationary member, wherein the pair of second stationary members and the second movable member stick out upward from the surface of the substrate 3 through the aperture 3B formed in the substrate 3 when the blood sugar level-measuring unit 2 is attached to the mount table 11. As understood from FIG. 4, a part of the calibrating liquid-supplying channel 5, which is connected to a branch of the Y-shaped tube and which runs to the calibrating-liquid tank 1G, is placed between one second stationary member 15 and the second movable member 16, while a part of the second diluent-supplying channel 6A, which is connected to the third branch of the Y-shaped tube, is placed between the other second stationary member 15 and the second movable member 16. When the second movable member 16 moves, for example, to the other second stationary member 15, and the second movable member 16 and the other second stationary member 15 pinch and compress the part of the second diluent-supplying channel 6A, the second diluent-supplying channel 6A is blocked up, which in turn realizes state (b) in which the calibrating liquid stored in the calibrating liquid tank 1G can be transferred to the first flow path changeover switch 1B. On the other hand, when the second movable member 16 moves to the one second stationary member 15, and the second movable member 16 and the other second stationary member 15 pinch and compress the part of the calibrating liquid-supplying channel 5, the calibrating liquid-supplying channel 5 is blocked up, which realizes the state (a) in which the second diluent-supplying channel 6A communicates with the section of the calibrating liquid-supplying channel 5, which section is between the second flow path changeover switch 1C and the first flow path changeover switch 1B.

As mentioned above, the second flow path changeover switch 1C is not limited to the combination of the pair of the second stationary members 15 and the second movable member 16, as long as the switch is capable of changing the ways of the communication. For example, other valves, such as a cross valve, two 2-way valves, or a rotary valve, may be used.

In the following paragraphs mixer 7 is described in detail.

Various mechanical structures may be employed for the mixer 7, as long as they are capable of mixing blood transferred through the blood-transferring channel 4B with a diluent, for example a buffer, supplied through the diluent-supplying channel 6. Because the fluid channel between the mixer 7 and the glucose sensor 4A is short in the blood sugar level-measuring unit 2, mechanical structures capable of mixing the blood with the diluent sufficiently until the sample liquid reaches the glucose sensor 4A should preferably be employed.

Figure 6:
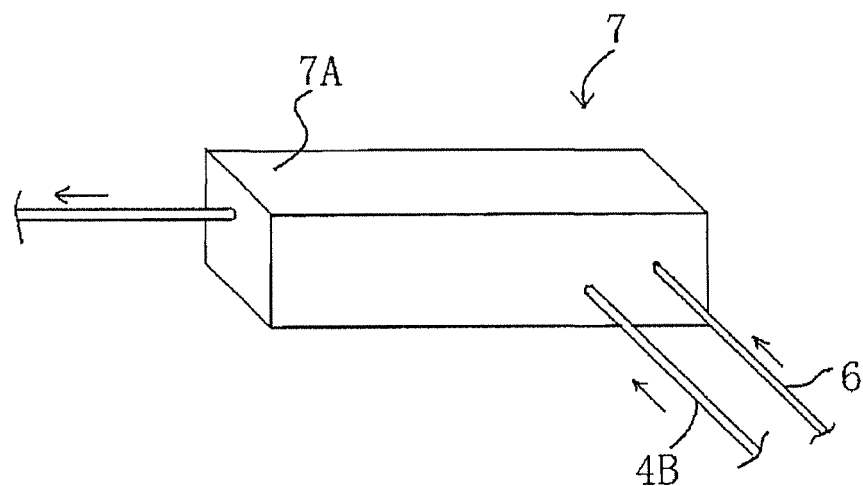
FIG. 6 is a schematic representation of a mixer of the blood sugar level-measuring unit according to the present invention.
Figure 7:
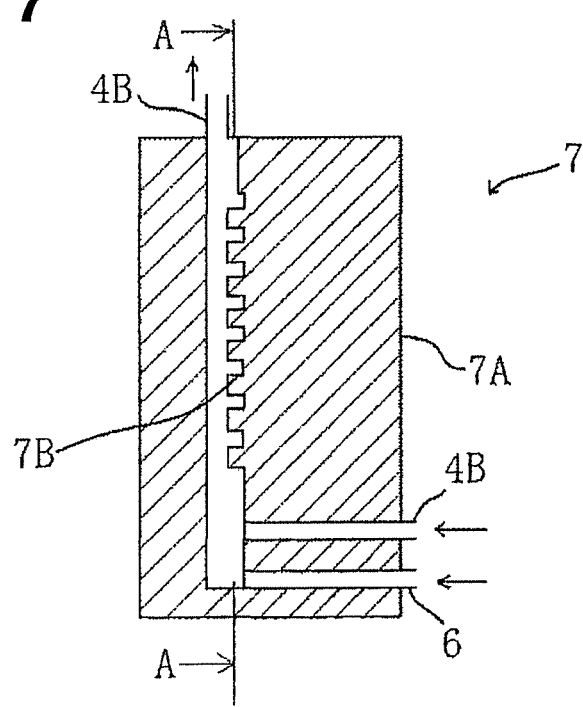
FIG. 7 is a schematic view showing the structure of a section of the mixer of the blood sugar level-measuring unit according to the present invention.
Figure 8:
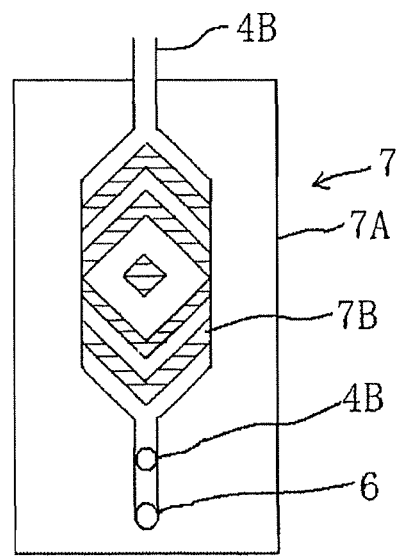
FIG. 8 is a schematic sectional view taken along line A-A in FIG. 7, showing another section of the mixer.

An example of a mixer 7 may be is shown in FIGS. 6-8.

As shown in FIGS. 6-8, the mixer 7 has a rugged part 7B comprised of continuous alternate projections and depressions running in the direction of fluid flow, which rugged part is formed in the inside face of a wall that defines, together with the other walls, an inner fluid flow space of the mixer proper 7A in the shape of a rectangular parallelepiped. As shown in FIG. 8, which is a sectional view taken along line A-A in FIG. 7, the rugged part 7B has a central portion in the form of diamonds. In more detail, the rugged part 7B has, in the direction of fluid flow, a V-shaped rugged portion comprising alternate V-shaped projections and V-shaped depressions first. In other words, the first portion of the rugged part has several V-shaped projections and several V-shaped depressions each between adjacent V-shaped projections. Next comes the central portion, which is followed by a reverse V-shaped rugged portion comprised of several projections in the shaped of a reverse V and several reverse V-shaped depressions each between adjacent reverse V-shaped projections. The diluent-supplying channel 6 and the blood-transferring channel 4B communicate with the inner fluid flow space.

Blood and a diluent introduced into the inner fluid flow space of the mixer proper 7A strike against the first projection of the rugged part 7B, which disturbs the flow of the blood and that of the diluent. The disturbed flows of the blood and the diluent climb over the first projection and fall into the adjacent depression. In the depression the next projection makes the flow of the blood and that of the diluent collide, and the flows are disturbed again. Also, the flow of the blood and that of the diluent are divided into a flow component running straight and flow components each running aslant along the walls of the V, since the rugged part 7B has the V-shaped rugged portion and the reverse V-shaped rugged portion. This division of the flows also creates disturbed flows of the blood and the diluent. The repetition of the disturbances, caused by crashes of the blood and the diluent against the projections and the divisions of the flows into the straightly running components and the aslant running components, mixes the blood and the diluent.

Figure 12:
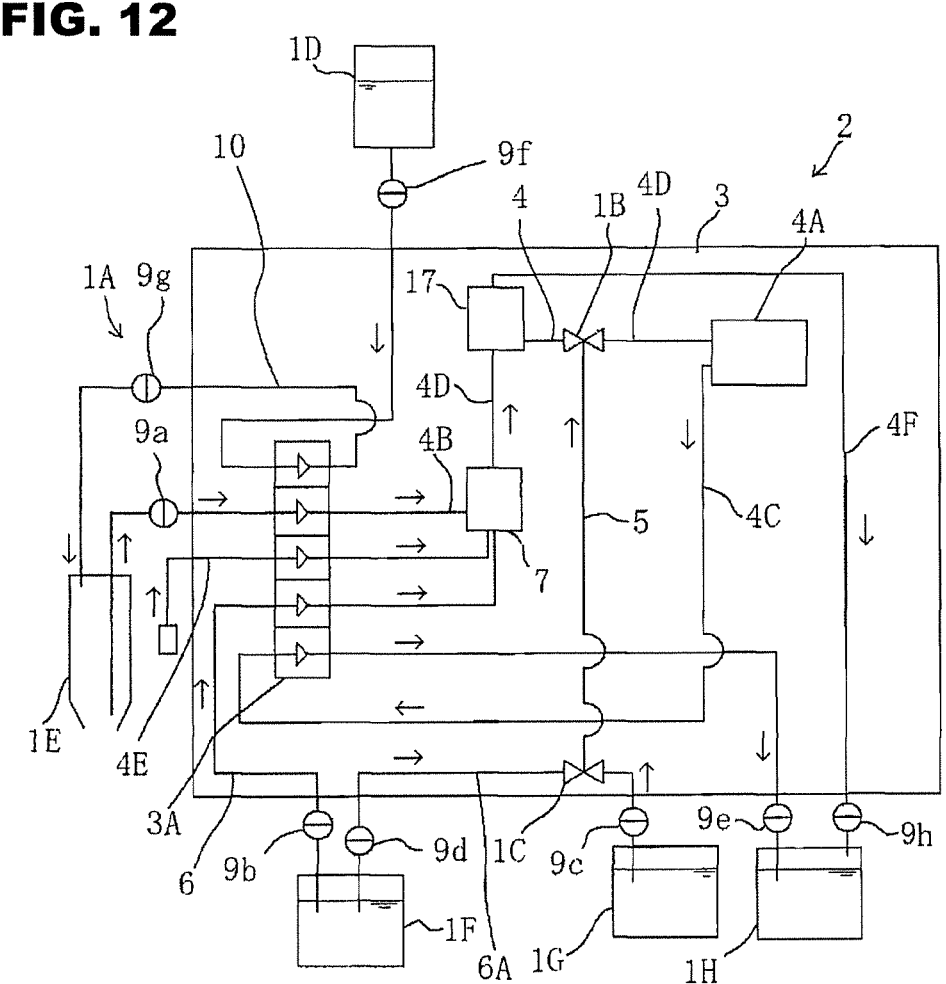
FIG. 12 is a block diagram illustrating an example of the blood sugar level-measuring unit according to an embodiment of the present invention.

In this embodiment, blood and a diluent are introduced into the mixer 7. However, the mixer is not limited to this embodiment. For example, a gas inert to blood and diluents, such as air, may be introduced, to mix blood and a diluent and to improve the efficiency of the mixing. FIG. 12 illustrates an example of the latter embodiment. This example further has a gas channel 4E on the substrate 3 in addition to the elements of the embodiment shown in FIG. 3. The gas channel 9E, as well as the blood-transferring channel 4B, is a flexible tube. The gas channel 4E is squeezed by the rollers in the window for the rollers 3A, whereby a gas, such as air, in the channel is sent toward the mixer 7. The air is mixed with a diluent in the mixer 7 or upstream of the mixer 7, and blood is further added. In this embodiment, a gas-liquid separator 17 is disposed downstream of the mixer 7, and the liquid, which is a mixture of blood and a diluent, and a gas are separated. The separated gas together with superfluous liquid is discharged through a gas-discharging channel 4F. Sending air to the mixer 7 in this way improves the efficiency of mixing blood and a diluent. It also shortens the time period for which sampled blood is in the mixer 7 and the sample liquid-transferring channel 4D, which makes it possible to measure sampled blood quickly.

Figure 13:
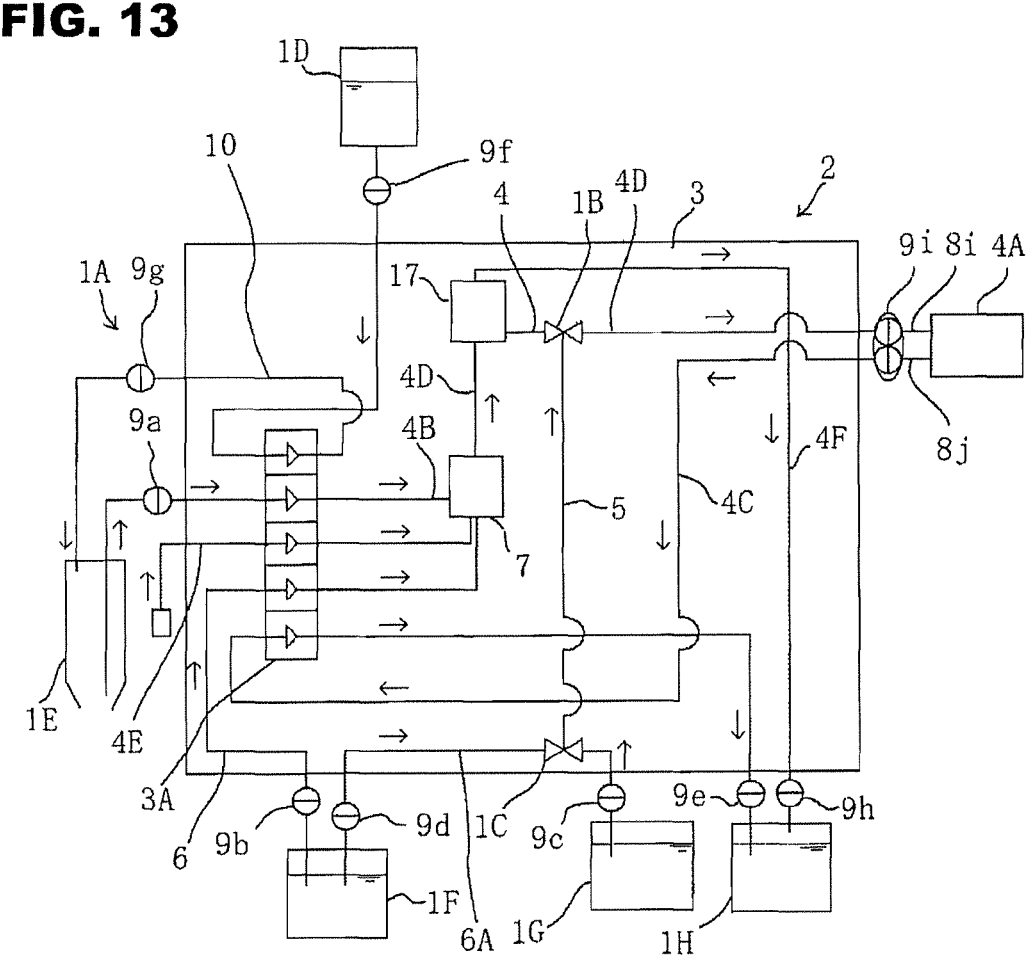
FIG. 13 is a block diagram illustrating another example of the blood sugar level-measuring unit according to an embodiment of the present invention.

The embodiment shown in FIG. 13 is an example of a biological component-measuring unit which does not have a sensor 4A interposed in the fluid channels on the substrate 3, as shown in FIG. 11, but a gas channel 4E and a gas-liquid separator 17 such as those explained above. This embodiment is capable enjoying both of the advantages of the embodiment shown in FIG. 11 and those of the example in FIG. 12.

Figure 9:
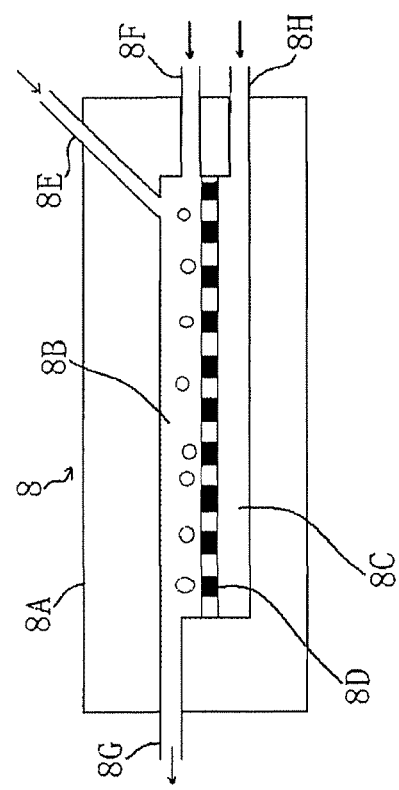
FIG. 9 is a schematic illustration showing the structure of a section of a variation of the mixer of the blood sugar level-measuring unit according to the present invention has.

The mixer 7 capable of expediting the mixing of blood with a diluent by introducing air into it, as explained above, may employ, for example, the structure of a mixer 8 shown in FIG. 9. As illustrated in FIG. 9, the mixer 8 has a mixing room 8B and a gas room 8C inside the mixer proper 8A in the shape of a rectangular parallelepiped. Inside the mixing room 8B, a gas-permeable partition 8D is disposed along the flow of the liquid or a gas. The gas-permeable partition 8D divides the inside space of the mixer proper 8A into the mixing room 8B and the gas room 8C. There is no special limitation on the gas-permeable partition 8D, as long as it has a structure allowing fine gas bubbles to spout into the mixing room 8B. The gas-permeable partition may be a porous plate-like member, specific examples of which may include porous hydrophobic polymer films, porous ceramic plates, and sponges made of synthetic resins.

The mixing room 8B is provided with a diluent path 8E through which a diluent supplied through the diluent-supplying channel 6 is introduced, a body fluid path 8F through which blood transferred through the blood-transferring channel 4B is introduced, and an outlet 8G that is connected to the sample liquid-transferring channel 4D with a gas-liquid separator 17 in between. The diluent path 8E and the body fluid path 8F should be disposed at a side of the mixer proper 8A, opposite the side at which the outlet 8G is placed.

The gas room 8C is provided with a gas inlet 8H through which a gas, such as air, is introduced into and flows through the gas room 8C.

A mixer 8 is described below. First, a diluent and blood are introduced into the mixing room 8B respectively through the diluent path 8E and the body fluid path 8F. On the other hand, air is introduced into the gas room 8C through the gas inlet 8H. The air having been introduced into the gas room 8C turns into fine air bubbles when the air passes through the gas-permeable partition 8D. These fine air bubbles are introduced into the mixing room 8B, and the introduced fine air bubbles stir the diluent and the blood that have also been introduced. The blood is sufficiently mixed with the diluent by the stirring, and the well-mixed fluid is drawn from the mixing room 8B through the outlet 8G.

The mixed diluent and blood is separated from fine gas bubbles by the gas-liquid separator provided downstream of the outlet 8G of the mixer 8, or next to the mixer 8.

By neatly arranging all the members and parts that contact fluids, such as a catheter 1E, a physiological saline tank 1D, a diluent tank 1F, a calibrating liquid tank 1G, and a waste liquid tank 1H, on the substrate, an example of the medical support instrument kit according to the present invention is prepared. By sterilizing this medical support instrument kit with a sterilizer such as ethylene oxide and packing the sterilized kit with a packing material in an isolated and sterile condition, or by packing the medical support instrument kit with a packing material in an isolated condition and sterilizing it with a sterilizer such as ethylene oxide, a package of the medical support instrument is prepared.

Below, it is explained how an artificial endocrine pancreas device to which the blood sugar level-measuring device 2 according to the present invention has been attached works.

(1) How to Measure Glucose

Before beginning an operation of the artificial endocrine pancreas device, the blood sugar level-measuring unit 2 is attached to the artificial endocrine pancreas device proper 1.

Specifically, the attaching pins 12 projecting from the mount table 11 are inserted into the holes for attachment 3C, and the abutment of the attaching rods to the attaching pins makes the substrate 3 firmly attached to the mount table 11. Then, the fluid channels on the substrate 3 are respectively connected to the physiological saline tank 1D, the catheter 1E, the diluent tank 1F, the calibrating liquid tank 1G, and the waste liquid tank 1H. The fluid channels are set to the roller pump, the first flow path changeover switch 1B, and the second flow path changeover switch 1C. These settings are made by connecting the respective connectors of the fluid channels with the connectors fixed to the ends of the fluid channels appended to the blood sugar level-measuring unit 2. The connection between the connectors is a very easy operation. The channel arranging and connecting operations for the artificial endocrine pancreas device are thus finished. In this embodiment, because the blood sugar level-measuring unit 2 is provided with the substrate 3 and the glucose-measuring fluid 4, it is not necessary for the operator to dispose and connect the fluid channels one by one, but just to attach the substrate 3 onto the artificial endocrine pancreas device proper 1. This unit is capable of simplifying the required operations such as disposing channels, improving workability, and decreasing the amount of work in an unhygienic condition caused by dirt of the fluid channels. Also, the fluid channels can be set to the roller pump mounted on the mount table 11 of the endocrine pancreas device, very easily by a single operation.

The catheter 1E of the artificial endocrine pancreas device is kept in the body of a patient. Then, as shown in FIG. 3, a heparin-containing physiological saline is transferred to the catheter 1E, which is a double lumen catheter, from the physiological saline tank 1D. Blood sampled through this catheter 1E is mixed with the heparin-containing physiological saline within this catheter 1E. The heparin-containing blood within the catheter is forcibly transferred through the blood-transferring channel 4B, which is squeezed by the rollers of the fluid transfer structure, to the mixer 7.

On the other hand, a diluent is transferred through the diluent-supplying channel 6 from the diluent tank 1F by the squeezing of the rollers 1A. The transferred diluent is sent to the mixer 7. In the mixer 7, as shown in FIGS. 7 and 8, the blood and the diluent are being mixed while striking against the rugged part 7B. A sample liquid is prepared by this mixing.

At this time, the first flow path changeover switch 1B blocks communication between the sample liquid-transferring channel 4D and the calibrating liquid-supplying channel 5, while connecting the blood-transferring channel 4B with the sample liquid-transferring channel 4D, which is state (1). Therefore the sample liquid flows through the sample liquid-transferring channel 4D, and enters the glucose sensor 4A where the glucose included in the sample liquid is measured. The data of the amount of glucose measured are transferred to a controller of the artificial endocrine pancreas device proper 1, which controller is not shown in the figures.

On the other hand, the sample liquid after the measurement is discharged to the outside of the glucose sensor 4A by the squeezing of the rollers 1A. The discharged sample liquid is transferred through the waste liquid-transferring channel 4C to the waste liquid tank 1H, in which the discharged sample liquid is stored.

In this embodiment, the blood sugar level-measuring unit 2 is provided with the substrate 3 and the glucose-measuring fluid 4. In other words, the fluid channels are arranged on the substrate prior to the commencement of, for example, the glucose measurement operation. Therefore it is not necessary for the operator to dispose and connect the fluid channels one by one, but just to attach the substrate onto the artificial endocrine pancreas device proper. The employment of this unit makes it possible to simplify conventionally required operations such as disposing channels, and improve workability. Because the use of this unit simplifies operations such as disposing channels, it also decreases the amount of work in an unhygienic condition caused by dirt of the fluid channels. In summary, the present invention provides the blood sugar level-measuring unit 2, which is capable of improving workability, and with which the clinical examiner is able to measure blood sugar levels by hygienic operation.

After the measurement of the glucose of the patient is completed in this way, the catheter 1E that has been kept in the patient's body is taken out. The fluid channels on the substrate 3 are detached from the physiological saline tank 1D, the catheter 1E, the diluent tank 1F, the calibrating liquid tank 1G, and the waste liquid tank 1G respectively, after, if necessary, the patient's blood remaining in the catheter and the fluid channels are discharged to the waste liquid tank 1H. The step of removing the substrate 3 from the artificial endocrine pancreas device proper is thus completed.

Because the substrate is provided with the fluid channels in advance, all that the operator has to do after the measurement of glucose is to detach the substrate from the artificial endocrine pancreas device proper; s/he does not have to detach the pipes of the used blood sugar level-measuring unit 2, which enables him/her to throw away the blood sugar level-measuring unit 2 without contacting fluids, such as body fluids, adhering to the elements of the units such as the pipes. Therefore also from this point of view, the present invention is capable of improving workability by providing a blood sugar level-measuring unit 2 that the operator is able to handle hygienically.

(2) How to Wash the Glucose Sensor 4A

The blood sugar level-measuring unit 2 is attached to the artificial endocrine pancreas device proper 1 in the same way as in the measurement of glucose explained above. It is optional to keep the catheter in the patient's body.

First, a diluent is transferred from the diluent tank 1F through a second diluent-supplying channel 6A via the second flow path changeover switch 1C and the first flow path changeover switch 1B, as shown in FIG. 3. The diluent is sent from the second diluent-supplying channel 6A toward the sample liquid-transferring channel 4D to the calibrating liquid-supplying channel 5 by the second flow path changeover switch 1C.

Then, the first flow path changeover switch 1B chooses the flow path to the sample liquid-transferring channel 4D, whereby the diluent having flowed through the second diluent-supplying channel 6A and the calibrating liquid-transferring channel 5 is sent into the glucose sensor 4A through the sample liquid-transferring channel 4D. The inside of the glucose sensor 4A is washed with the diluent that has been transferred.

The used diluent is discharged from the glucose sensor 4A to the outside thereof by the squeezing of the rollers 1A. The discharged diluent is sent through the waste liquid-transferring channel 4C to the waste liquid tank 1H, in which the diluent is stored.

The artificial endocrine pancreas device whose glucose sensor 4 has been washed is used to measure the glucose of a patient. Alternatively, the blood sugar level-measuring unit 2 is removed from the device, and the operation of the device is stopped.

(3) How to Calibrate the Glucose Sensor 4A

The blood sugar level-measuring unit 2 is attached to the artificial endocrine pancreas device proper 1 in the same way as in the measurement of glucose explained above. It is optional to keep the catheter in the patient's body.

Then, a calibrating liquid is sent from the calibrating liquid tank 1G to the calibrating liquid-transferring channel 5 by the second flow path changeover switch 1C, and transferred through the calibrating liquid-transferring channel toward the sample liquid-transferring channel 4D.

Next, the first flow path changeover switch 1B closes the flow path that communicates with the fluid channel connected to the mixer, and makes the fluid channel from the switch 1B to the glucose sensor 4A communicate with the calibrating liquid-transferring channel 5. The calibrating liquid thus transferred from the calibrating liquid channel 5 to the sample liquid-transferring channel 4D is sent into the glucose sensor 4A. During the calibration, the glucose sensor 4 is obtaining data in the state that the calibrating liquid is being sent to the sensor. The obtained data are sent to the controller of the artificial endocrine pancreas device proper 1, which controller is not shown in the figures. Until the controller finds that the data reach a predetermined calibrated value, the calibrating liquid is continuously sent to the sensor and the sensor continues obtaining data.

After the calibration is completed, the calibrating liquid remaining in the glucose sensor 4A is discharged to the outside, by the squeezing of the rollers 1A. The discharged calibrating liquid is sent through the waste liquid-transferring channel 4C to the waste liquid tank 1H, in which the calibrating liquid is stored.

The artificial endocrine pancreas device whose glucose sensor 4 has been calibrated is used to measure the glucose of a patient. Alternatively, the blood sugar level-measuring unit 2 is removed from the device, and the operation of the device is stopped.

When a blood sugar level-measuring unit 2 is used in clinics and hospitals that have strict hygienic standards, a blood sugar level-measuring unit packed with a packing material such as a bag and sealed in an isolated condition, or a blood sugar level-measuring unit package, should be employed. The blood sugar level-measuring unit package comprises a blood sugar level-measuring unit contained in a packing material in an isolated condition. A blood sugar level-measuring unit 2 may be sterilized with, for example, ethylene oxide prior to the packing, or it may be sterilized, together with the packing material, after it is packed. The blood sugar level-measuring unit 2 may be sterilized by common sterilizing methods, such as heating or irradiation with ultraviolet rays.

The packing material may be anything as long as it is capable of containing the blood sugar level-measuring unit 2. Examples may be bags made of resins such as polyethylene or polypropylene.

Because a blood sugar level-measuring unit is kept sterile in a package of a blood sugar level-measuring unit, the clinical examiner is capable of operating an artificial endocrine pancreas device just by taking the blood sugar level-measuring unit out of the package and attaching it to the device artificial endocrine pancreas proper. Also after the operation of the artificial endocrine pancreas device, the used blood sugar level-measuring unit may be detached from the device proper and discarded. Therefore the present invention provides a safe package of a blood sugar level-measuring unit whose operability is excellent, which is hygienic, and which gives the operator fewer opportunities to contact patients' body fluids.

The blood sugar level-measuring unit in this embodiment is used to measure glucose in blood. However, it may measure body fluids other than blood from which the unit is capable of measuring glucose. Examples of such body fluids may include urine, sweat, and intercellular liquid.

In the embodiment explained hereinbefore is employed a multiple roller device as a liquid transfer means. However, a roller device having a single rotating shaft, and a single elongated roller supported by the shaft with its axis parallel to the axis of the rotating shaft may be employed. In the latter case, the roller device is so designed that fluids in all the fluid channels through which the fluids have to be transferred are transferred by the squeezing of the single roller.

Also, in the foregoing embodiment, the blood-sampling instrument, such as a catheter, is provided separately, in addition to the artificial endocrine pancreas proper and the blood sugar level-measuring unit. However, the blood-sampling instrument may be included in, for example, the blood sugar level-measuring unit in advance.

I claim:

1. A biological component-measuring unit comprising:
  a substrate detachably mountable on a medical support device;
  fluid channels arranged on a surface of the substrate, the fluid channels comprising a biological component-measuring channel, a first diluent-supplying channel, a gas channel configured to introduce a gas and a gas-liquid separator, all of which are arranged on the surface of the substrate; and
  an engaging mechanism configured to detachably engage with the medical support device so that the biological component-measuring unit is attached to and detached from the medical support device, wherein:
  the biological component-measuring channel includes:
    a first fluid transferring section configured to be engaged with and actuated by a first fluid transfer structure disposed on the medical support device and transfer a sample fluid in one direction in cooperation with the first fluid transfer structure, when the biological component-measuring unit is mounted on the medical support device,
  the first diluent-supplying channel includes:
    a first connector configured to be attached to and detached from a diluent-drawing channel through which a diluent stored in a diluent storage tank is drawn;
    a second fluid transferring section configured to be engaged with and actuated by a second fluid transfer structure disposed on the medical support device and transfer the diluent in one direction in cooperation with the second fluid transfer structure, when the biological component-measuring unit is mounted on the medical support device,
  the first diluent-supplying channel is configured to supply the diluent to the biological component-measuring channel within the biological component-measuring unit so that the diluent is mixed with the sample fluid before the sample fluid is supplied to the biological component sensor,
  the gas channel includes:
    a third fluid transferring section configured to be engaged with and actuated by a third fluid transfer structure disposed on the medical support device and transfer the gas through the gas channel in one direction in cooperation with the third fluid transfer structure, when the biological component-measuring unit is mounted on the medical support device, the gas channel is configured to supply the gas to the first diluent-supplying channel, the gas-liquid separator is disposed at a part downstream of a point where the diluent and the fluid are mixed and upstream of the biological component sensor, a window is formed in the substrate for receiving the first fluid transfer structure, the window being an opening passing through the substrate, the first fluid transferring section passes over the window, the second fluid transferring section passes over the window, and the third fluid transferring section passes over the window.

2. The biological component-measuring unit according to claim 1, wherein the biological component-measuring channel further includes:
- a second connector configured to be attached to and detached from a body fluid-drawing channel for drawing the sample fluid that has been sampled through a body fluid sampler;
- a third connector configured to be attached to and detached from a sample-introducing channel attached to a biological component sensor,
- a fourth connector configured to be attached to and detached from a return channel from the biological component sensor;
- a sample-discharging channel arranged on the surface of the substrate coupled to the fourth connector and configured to receive the sample fluid discharged from the biological component sensor; and
- an outlet port configured to discharge the sample fluid received from the biological component sensor to outside the biological component-measuring unit, wherein a part of the sample-discharging channel passes over the window.

3. The biological component-measuring unit according to claim 2, wherein:
- the fluid channels further comprise a calibrating liquid-supplying channel arranged on the surface of the substrate,
- the calibrating liquid-supplying channel includes a fifth connector configured to be attached to and detached from a calibrating liquid-drawing channel attached to through which a calibrating liquid stored in a calibrating liquid storage tank is drawn,
- the calibrating liquid-supplying channel is configured to supply the calibrating liquid to the biological component-measuring channel within the biological component-measuring unit so that the calibrating liquid is supplied to the biological component sensor,
- the biological component-measuring channel includes a first fluid channel make-and-break section and a second fluid channel make-and-break section,
- the first fluid channel make-and-break section is configured to be engaged and actuated by a first fluid channel make-and-break switch disposed on the medical support device and make or break a flow of the sample fluid in cooperation with the first fluid channel make-and-break switch, when the biological component-measuring unit is mounted on the medical support device,
- the second fluid channel make-and-break section is configured to be engaged and actuated by a second fluid channel make-and-break switch disposed on the medical support device and make or break a flow of the diluent in cooperation with the second fluid channel make-and-break switch, when the biological component-measuring unit is mounted on the medical support device,
- the first fluid channel make-and-break section disposed on the biological component-measuring channel at a junction where the calibrating liquid-supplying channel is connected to the biological component-measuring channel,
- the second fluid channel make-and-break section is disposed on the calibrating liquid-supplying channel at a junction where the calibrating liquid-supplying channel is connected to a second diluent-supplying channel,
- a first aperture and a second aperture are formed in the substrate, the first and second apertures being opening passing through the substrate, and
- the first fluid channel make-and-break section passes over the first aperture and the second fluid channel make-and-break section passes over the second aperture.

4. The biological component-measuring unit according to claim 3, wherein the first and second fluid channel make-and-break sections are configured such that, in cooperation with the first and second fluid channel make-and-break switches:
- the flow of the sample fluid through the biological component-measuring channel is broken at the first fluid channel make-and-break section when the flow of the diluent through the second diluent-supplying channel is made at the second fluid channel make-and-break section, and
- the flow of the sample fluid through the biological component-measuring channel is made at the first fluid channel make-and-break section when the flow of the diluent through the second diluent-supplying channel is broken at the second fluid channel make-and-break section.

5. The biological component-measuring unit according to claim 1, wherein the fluid channels further comprise a mixing gadget arranged on the surface of the substrate for mixing the sample fluid flowing through biological component-measuring channel with the diluent supplied through the first diluent-supplying channel.

6. The biological component-measuring unit according to claim 1, wherein the window is configured to receive an actuator of the first fluid transfer structure.

7. The biological component-measuring unit according to claim 1, wherein the engaging mechanism includes at least one of holes passing through the substrate and attaching rods fixed to edges of the substrate.

8. The biological component-measuring unit according to claim 1, further comprising a biological component sensor disposed on the surface of the substrate, connected to the biological component-measuring channel and configured to measure a biological component included in the sample fluid, wherein the biological component-measuring channel further includes:
- a second connector configured to be attached to and detached from a body fluid-drawing channel for drawing the sample fluid that has been sampled through a body fluid sampler, the biological component-measuring channel being coupled to the second connector;
- a sample-discharging channel through which the sample fluid is discharged from the biological component sensor; and
- an outlet port connected to the sample-discharging channel and configured to discharge the sample fluid from the biological component sensor.

9. The biological component-measuring unit according to claim 8, wherein the fluid channels further comprise a mixing gadget arranged on the surface of the substrate for mixing the sample fluid flowing through biological component-measuring channel with the diluent supplied through the first diluent-supplying channel.

10. The biological component-measuring unit according to claim 8, wherein:
   the fluid channels further comprise a calibrating liquid-supplying channel arranged on the surface of the substrate,
   the calibrating liquid-supplying channel includes a fifth connector configured to be attached to and detached from a calibrating liquid-drawing channel attached to through which a calibrating liquid stored in a calibrating liquid storage tank is drawn,
   the calibrating liquid-supplying channel is configured to supply the calibrating liquid to the biological component-measuring channel within the biological component-measuring unit so that the calibrating liquid is supplied to the biological component sensor,
   the biological component-measuring channel includes a first fluid channel make-and-break section and a second fluid channel make-and-break section,
   the first fluid channel make-and-break section is configured to be engaged and actuated by a first fluid channel make-and-break switch disposed on the medical support device and make or break a flow of the sample fluid in cooperation with the first fluid channel make-and-break switch, when the biological component-measuring unit is mounted on the medical support device,
   the second fluid channel make-and-break section is configured to be engaged and actuated by a second fluid channel make-and-break switch disposed on the medical support device and make or break a flow of the diluent in cooperation with the second fluid channel make-and-break switch, when the biological component-measuring unit is mounted on the medical support device,
   the first fluid channel make-and-break section disposed on the biological component-measuring channel at a junction where the calibrating liquid-supplying channel is connected to the biological component-measuring channel,
   the second fluid channel make-and-break section is disposed on the calibrating liquid-supplying channel at a junction where the calibrating liquid-supplying channel is connected to a second diluent-supplying channel,
   a first aperture and a second aperture are formed in the substrate, the first and second apertures being opening passing through the substrate, and
   the first fluid channel make-and-break section passes over the first aperture and the second fluid channel make-and-break section passes over the second aperture.

11. The biological component-measuring unit according to claim 10, wherein the first and second fluid channel make-and-break sections are configured such that, in cooperation with the first and second fluid channel make-and-break switches:
   the flow of the sample fluid through the biological component-measuring channel is broken at the first fluid channel make-and-break section when the flow of the diluent through the second diluent-supplying channel is made at the second fluid channel make-and-break section, and
   the flow of the sample fluid through the biological component-measuring channel is made at the first fluid channel make-and-break section when the flow of the diluent through the second diluent-supplying channel is broken at the second fluid channel make-and-break section.

* * * * *